United States Patent
Papadopoulos et al.

(10) Patent No.: US 9,757,485 B2
(45) Date of Patent: Sep. 12, 2017

(54) SYSTEM AND METHOD FOR FLUID STERILIZATION

(71) Applicant: Michael Papadopoulos, Seal Beach, CA (US)

(72) Inventors: Michael Papadopoulos, Seal Beach, CA (US); Christian Papadopoulos, Seal Beach, CA (US); Mark Papadopoulos, Seal Beach, CA (US); James Ray Lewis, Pasadena, CA (US)

(73) Assignee: Michael Papadopoulos, Seal Beach, CA (US)

( * ) Notice: Subject to any disclaimer, the term of this patent is extended or adjusted under 35 U.S.C. 154(b) by 0 days.

(21) Appl. No.: 15/249,097

(22) Filed: Aug. 26, 2016

(65) Prior Publication Data

US 2017/0143858 A1 May 25, 2017

Related U.S. Application Data

(60) Provisional application No. 62/211,576, filed on Aug. 28, 2015.

(51) Int. Cl.
*A61L 2/04* (2006.01)
*A61L 2/24* (2006.01)
(Continued)

(52) U.S. Cl.
CPC ...... *A61L 2/04* (2013.01); *A61L 2/24* (2013.01); *B01D 3/06* (2013.01); *B01D 3/42* (2013.01); *C02F 1/008* (2013.01); *C02F 1/02* (2013.01); *C02F 1/06* (2013.01); *A61L 2202/14* (2013.01); *C02F 2201/005* (2013.01); *C02F 2209/02* (2013.01); *C02F 2209/03* (2013.01); *C02F 2303/04* (2013.01); *Y02W 10/37* (2015.05)

(58) Field of Classification Search
CPC .......... A61L 2/04; A61L 2/24; A61L 2202/14; C02F 1/008; C02F 1/06; C02F 2203/04; C02F 2201/005; C02F 2209/02; C02F 2209/03
See application file for complete search history.

(56) References Cited

U.S. PATENT DOCUMENTS

| 3,718,082 A | 2/1973 | Lipoma |
| 3,835,762 A | 9/1974 | Rambaud |

(Continued)

FOREIGN PATENT DOCUMENTS

| WO | WO 2006/006946 | 1/2006 |
| WO | WO 2013090947 | 6/2013 |

*Primary Examiner* — Timothy Cleveland
(74) *Attorney, Agent, or Firm* — Tsircon Law, PC

(57) ABSTRACT

A system and method of fluid sterilization is provided, which incorporates a heating section to heat pressurized fluid above prescribed thresholds for temperature, pressure, and duration (e.g., dwell time) to achieve desired levels of sterilization, including a heat exchanger to both (a) preheat fluid prior to entering the heating section and (b) cool outflow of the heating apparatus, in which fluid travels through the apparatus by operating valves forward and aft of the heating section in a controlled sequence to facilitate flow through the system while maintaining prescribed pressure and temperature profiles. The system operates within prescribed ranges of pressure and temperature to achieve the desired level of sterilization without need of maintaining a fixed temperature or a fixed pressure within any portion of the system, including the heating section.

20 Claims, 24 Drawing Sheets

(51) Int. Cl.
  *C02F 1/02* (2006.01)
  *B01D 3/06* (2006.01)
  *B01D 3/42* (2006.01)
  *C02F 1/00* (2006.01)
  *C02F 1/06* (2006.01)

(56) References Cited

U.S. PATENT DOCUMENTS

| | | |
|---|---|---|
| 4,782,643 A | 11/1988 | Stark |
| 4,855,552 A | 8/1989 | Marceau et al. |
| 5,520,892 A | 5/1996 | Bowen |
| 7,018,592 B2 | 3/2006 | Bowen |
| 7,862,784 B2 | 1/2011 | Bowen |
| 9,056,145 B2 | 6/2015 | Bowen |
| 9,211,351 B2 | 12/2015 | Bowen |
| 2005/0019239 A1 | 1/2005 | Bowen |
| 2006/0018785 A1 | 1/2006 | Bowen |
| 2007/0131603 A1 | 6/2007 | Kantor et al. |
| 2007/0221362 A1 | 9/2007 | Stewart et al. |
| 2008/0107561 A1 | 5/2008 | Bowen |
| 2009/0152183 A1 | 6/2009 | Stewart et al. |
| 2009/0181139 A1 | 7/2009 | Farid |
| 2011/0042322 A1 | 2/2011 | Bowen |
| 2012/0015086 A1 | 1/2012 | Zeiler et al. |
| 2012/0118799 A1 | 5/2012 | Bowen |

SYSTEM AND METHOD FOR FLUID STERILIZATION

CROSS REFERENCE TO RELATED APPLICATION

This application claims the benefit of U.S. App. No. 62/211,576, filed Aug. 28, 2015, which is incorporated by reference.

FIELD OF THE INVENTION

The present invention relates generally to fluid purification and sterilization and, more particularly, to purification and sterilization by heating fluid above thresholds for temperature, pressure, and duration (e.g., dwell time).

BACKGROUND OF THE INVENTION

Fluid sterilization plays an important role across a wide spectrum of applications, to include personal, industrial, manufacturing, and medical applications. Generally speaking, sterilization is identified as a process that will make an object free of any living transmissible agent (such as fungi, bacteria, viruses, spore forms, microorganisms, prions, etc.). The object to be sterilized may be any of several types, including surfaces, a volume of fluid, or other materials in use or to be used in human or animal activities. Effectiveness of sterilization is generally referenced via a sterility assurance level (SAL).

Moreover, the issue of aqueous fluid sterilization is one of growing importance to both the developed and developing world alike. Complications resulting from contact with bacterially contaminated water are some of the leading causes of illness in the developing world. Further, it is one of the leading causes of death amongst children in the developing world.

Current challenges embodied in present sterilization operations of water leave much room for improvement. Most clean water systems today use sterilization processes such as reverse osmosis, membrane (filter) technology, or UV light technology. These systems require regular maintenance, a large amount of energy, and routine replacement of major components, such as membranes, filters or UV bulbs. As such, they are expensive to operate and maintain, particularly for high volume applications. Another solution involves the heating of the water to a high temperature as a means to sterilize, which typically requires large heat-sink apparatus to contain and cool the water after heating.

Both approaches necessitate the apparatus to be structurally large and generally immobile. Further challenges involve solutions using a non-continuous flow of the fluid, by-product being created by the process necessitating more maintenance, and the limitation to process only water.

Additionally, as invasive medical procedures become more commonplace and routine, the growing contact of foreign instruments with the relatively unprotected interior of human bodies greatly increases the need of proper instrument sterilization. Current solutions typically involve sterilization through immersion in disinfecting solutions (e.g., alcohol or bleach), ultrasonic methods (produce cavitation via high frequency sound waves) to clean, or exposure to high temperature in the form of high-pressure steam. These solutions have their limiting challenges: disinfecting solution methods produce harmful waste with limited re-use; the ultrasonic process is time intensive and demanding of both energy and maintenance; and high-pressure steam solutions can potentially damage sensitive and fragile equipment and special equipment with high pressure seals, etc. Most current solutions contain a number of moving parts, the addition of each creating the added issue of maintenance, and risk of possible contamination.

Further, contaminants such as "prions" are very difficult to kill and resistant to virtually all current sterilization methods. Prions are proteins that are folded in structurally distinct ways, which can be transmissible to other proteins, causing these other protein molecules to adopt such distinctive folding. Such misfolded protein replication within humans and other mammals can be harmful, particularly to brain and nervous tissue. This form of replication leads to disease that is similar to viral infection.

A protein as an infectious agent stands in contrast to all other known infectious agents, like viruses, bacteria, fungi, or parasites—all of which must contain nucleic acids (DNA, RNA, or both). In many instances, prions in mammals can have deleterious consequences, such as damage to brain and neural tissue, which are currently untreatable, other than complete removal of the infected tissue from the patient. Equipment and instruments used for such treatment must thereafter be considered contaminated.

Current procedures for decontaminating medical equipment are ineffective at reliably eliminating or inactivating prions to a medically acceptable level. As such, current protocols commonly call for disposal and destruction of medical equipment exposed to prions, which is an expensive proposition.

Therefore, it should be appreciated there remains a need for an apparatus and method which can produce sterile fluid for a variety of uses, such as, to sterilize contaminated instruments and equipment to a degree not possible with current approaches.

SUMMARY OF THE INVENTION

Briefly, and in general terms, the invention provides a system and method of fluid sterilization which incorporates a heating section to heat pressurized fluid above prescribed thresholds for temperature, pressure, and duration (e.g., dwell time) to achieve desired levels of sterilization, including a heat exchanger to both (a) preheat fluid prior to entering the heating section and (b) cool outflow of the heating apparatus, in which fluid travels through the apparatus by operating valves forward and aft of the heating section in a controlled sequence to facilitate flow through the system while maintaining prescribed pressure and temperature profiles. The system operates within prescribed ranges of pressure and temperature to achieve the desired level of sterilization without need of maintaining a fixed temperature or a fixed pressure within any portion of the system, including the heating section.

More specifically, in an exemplary embodiment, the system incorporates a plurality of valves coupled to a controller such as a computer, including valves disposed at inlet and outlet points of the heat exchanger and at inlet and outlet points of the heating apparatus. The valves are operated in a controlled sequence to enable effective operation of the system to include maintaining fluid within the heating assembly for the desired duration to achieve sterilization. Thereafter, inlet and outlet ports are opened in a sequenced manner to enable the fluid to exit heating assembly while creating a draw of received fluid from the heat exchanger into the heating apparatus. The system can utilize a controller that implements proprietary software for controlling system operations, including controlled sequence of the valves.

In a detailed aspect of an exemplary embodiment, the system can be operated free of pumps, while achieving the desired pressure levels due at least in part to controlled sequence operation of the valves via the controller. Inlet water pressure is preferably at a minimum level.

In another detailed aspect of an exemplary embodiment, the apparatus may further recirculate fluid to sterilize system pathways and/or may include an autoclave chamber to sterilize equipment.

In another detailed aspect of an exemplary embodiment, the apparatus may further include pipes running in parallel through the heat exchanger and the heating section.

For purposes of summarizing the invention and the advantages achieved over the prior art, certain advantages of the invention have been described herein. Of course, it is to be understood that not necessarily all such advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other advantages as may be taught or suggested herein.

All of these embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment disclosed.

BRIEF DESCRIPTION OF THE DRAWINGS

Embodiments of the present invention will now be described, by way of example only, with reference to the following drawings in which.

DETAILED DESCRIPTION OF THE PREFERRED EMBODIMENTS

The term "fluid" as used herein is defined to include any gas or liquid capable of flowing through the system, including water or aqueous solutions such as juice or milk, and liquids or gases with dissolved or suspended solids such as flue gas or crude oil or wastewater, e.g., black water or grey water.

Figure 1:
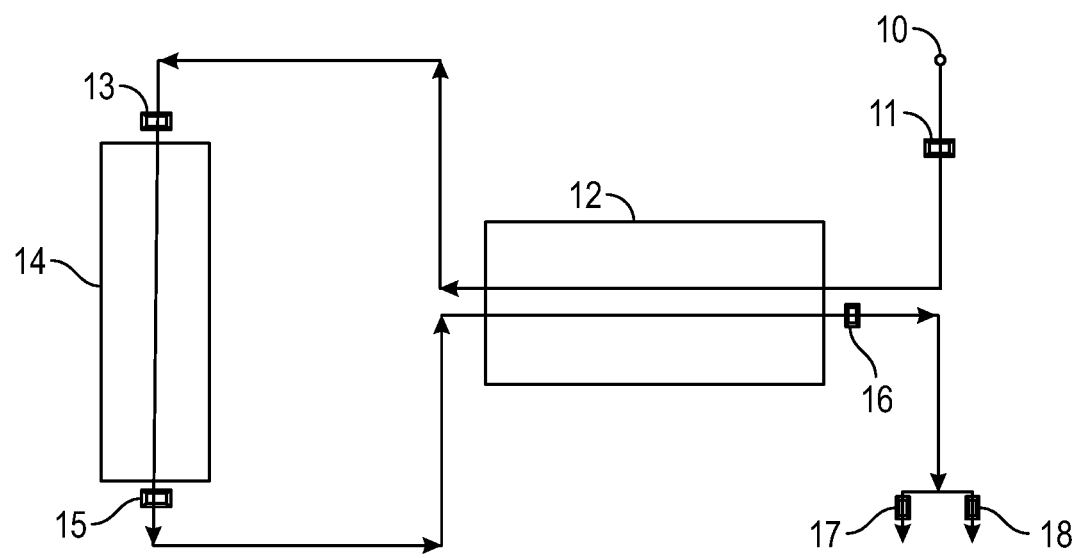
FIG. 1 is a simplified block diagram of a first embodiment of a fluid sterilization assembly in accordance with the present invention.
Figure 2:
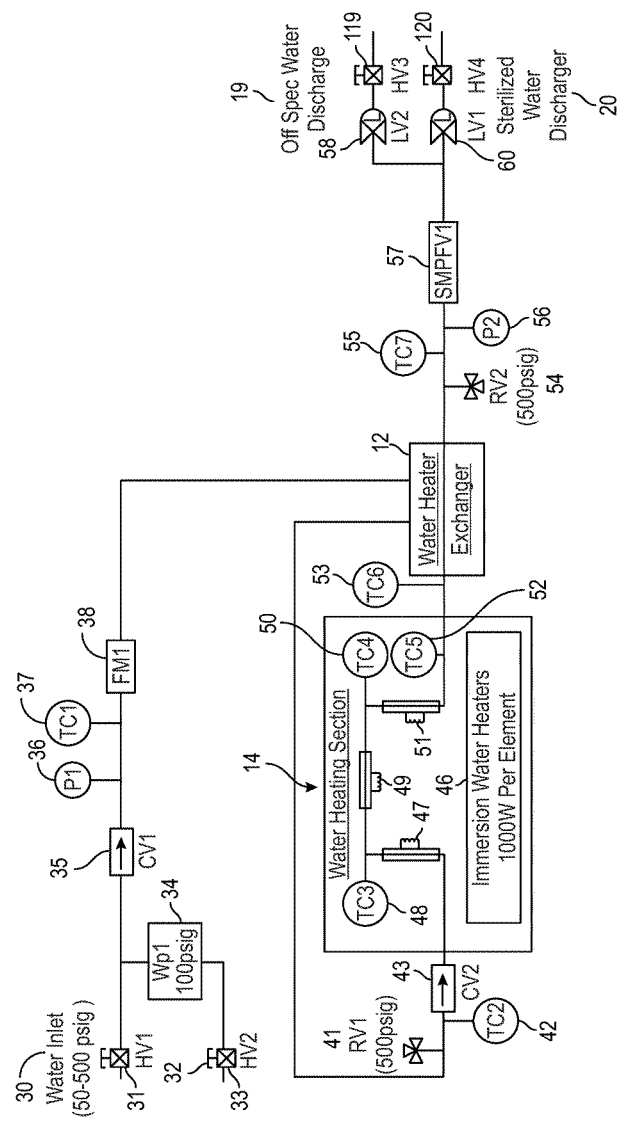
FIG. 2 is a simplified block diagram of a second embodiment of a fluid sterilization assembly in accordance with the present invention, incorporating electric immersion heaters as heating apparatus.

Referring now to the drawings, and particularly FIGS. 1 and 2, there is shown a fluid sterilization assembly usable for sterilizing water. A fluid source 10 is connected to an inlet of the assembly. The system uses high temperature to sterilize the fluid to a desired level. This sterilized fluid then has a variety of uses, one of which being the production of decontaminated drinking water no matter the level of biological contamination or source. Sterilization is achieved by passing the fluid through a heating element to super heat the fluid to such a degree as to sterilize any living transmissible agents. The system operates within prescribed ranges for pressure and temperature to achieve the desired level of sterilization without need of maintaining a fixed temperature or a fixed pressure within any portion of the system, including the heating section. Moreover, inlet pressure of the fluid enables flow through the system.

Operation of the assembly can include a start-up phase, a continuous flow phase and an operations phase. In the start-up phase, fluid is initially introduced into the system, sterilized, resides for a short time, and primes the system for continuous flow operation. In the operations phase, sterilized fluid is directed for use, e.g., see FIG. 23 for various operational states for the assembly.

The assembly in FIGS. 1 and 2 contains an inlet for the fluid, which comprises a valve assembly 11. The fluid continues along the flow path to a first (cool) path portion of a heat exchanger 12, in which the fluid is pre-heated, before it travels along the flow path to a heating section 14, where the fluid is heated to a prescribed temperature and pressure for a prescribed duration (e.g., dwell time) to sterilize the fluid to above a desired level. Thereafter, the fluid then travels along the flow path back through a second (hot) path portion of the heat exchanger 12 to cool before it exits the system. During the start-up phase, fluid exits the system through valve assembly 18 as off-spec discharge 19. During the operation phase, the fluid exits the system through valve assembly 17 as sterile fluid discharge 20. Discharge of fluid from the system can create a draw of more fluid into the system, to contribute to flow of contaminated fluid into the system, and discharge of sterilized fluid. Moreover, inlet pressure of the fluid enables flow through the system.

The exemplary embodiment utilizes several valves of different types at several dispositions in order to maintain a desired operating range of process variables, such as flow rate or pressure. The specific number, use, and disposition of valves in the embodiments herein is described for illustrative purposes only, and is not to be understood as limiting the present invention to these specific numbers, uses, or dispositions of valves. Various types of valves, including the check valves, proportional flow valves, solenoid valves, and relief valves described in the exemplary embodiment, may be added or removed at various dispositions in the system with similar functionality. For example, servo valves may be used in place of or in addition to latch valves described in the exemplary embodiment, and may be disposed anywhere along the flow path of the system, or may be eliminated from the system altogether. As another example, stepper motor proportional flow valves may be used in place of or in addition to pilot-operated proportional flow valves, used with or without pressure transducers or flow meters. Furthermore, the valves in the system may be actuated by hand, by spring, by solenoid, or by any other means of valve actuation. Similarly, the number and disposition of thermocouples, pressure transducers, and process sensors or other control-related apparatus other than valves may be altered from the descriptions herein without departing from the scope of the present invention. Moreover, the heating components can be insulated to inhibit radiant heat loss. Various forms of insulation can be used, such as, e.g., ceramic layer can be used, which can provide additional benefits. For example, immersion heaters can be provided with a ceramic coating, which can further inhibit scaling (build up) on the heaters, over extended use.

A controller or controllers 180, disposed internally or connected externally to the system, interfaces with the valves, transducers, thermocouples, or sensors in the system. The controller 180 in the exemplary embodiment is a digital computer comprised of a microprocessor that executes computer readable instructions to coordinate the operation of the system; however, any device capable of process control may be used, including, but not limited to, mechanical or pneumatic controllers, or analog electronic systems. The use of controllers could enable an operator to observe and manage the sterilization process (e.g., reading sensor data from a user interface or display, and opening or closing valves accordingly), or could enable the system to operate autonomously under prescribed operational guidelines. Controllers may be used to a limited degree, or may be used to such an extent that the system would merely need to be powered on in order to produce sterilized fluid according to specification. Embodiments of the system may be used without controllers, however, such that an operator could manually actuate valves and read sensors information, i.e., gauges or visual readouts or graphics.

More particularly, and with continued reference to FIG. 2, fluid enters the system from the inlet 30 through a hand valve (HV1) 31. In the exemplary embodiment, the fluid has a pressure between 50 psig and 500 psig, and travels through a check valve (CV1) 35, a pressure transducer (P1) 36, a thermocouple (TC1) 37, and a flow meter (FM1) 38. Additionally or alternatively, a pump 34 may be used to draw fluid from a reservoir or other source of unpressurized fluid through an inlet 32. Check valves are used to ensure unidirectional flow in the system, and pressure transducers and thermocouples, as well as other sensors, are used to monitor the dynamic properties of the fluid in the system. Flow meters are used to determine the rate of fluid passing through the system, which can be altered using proportional flow valves. The inlet fluid pressure defines the flow rate and the residence time at the sterilization temperature, according to the applicable sterilization temperature. Table 1, below, lists sterilization temperatures for given inlet pressure in an exemplary embodiment.

TABLE 1

| Inlet Pressure (psig) | Boiling Point (° C.) | Sterilization Temperature (° C.) |
|---|---|---|
| 10 | 115 | 108 |
| 50 | 147 | 140 |
| 100 | 170 | 163 |
| 200 | 198 | 191 |
| 300 | 216 | 209 |
| 400 | 231 | 224 |
| 500 | 254 | 243 |

Figure 6:
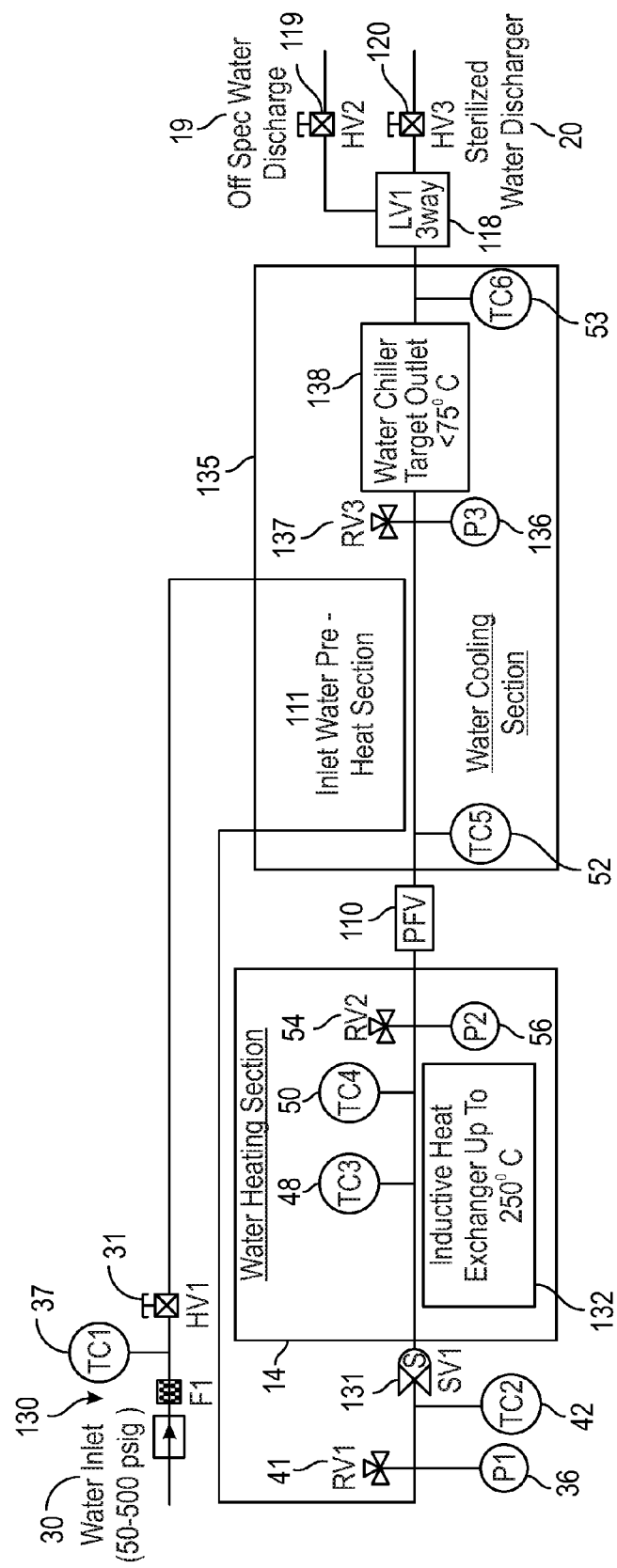
FIG. 6 is a simplified block diagram of a sixth embodiment of a fluid sterilization assembly in accordance with the present invention, incorporating a cooling section and an inductive heat exchanger as a heating element.

As the fluid enters the system, it may pass through a filter (F1) 130 (FIG. 6) for solid contaminants removal, before continuing into the heat exchanger 12. The heat exchanger 12 both (a) preheats fluid prior to entering the heating section 14 and (b) cools outflow of the heating section 14, by enabling heat transfer therebetween. In the exemplary embodiment, fluid enters the system at ambient, typically between 15° C. and 20° C., as measured by TC1 37 disposed along the flow path between the inlet 30 and the heat exchanger 12. The fluid then flows through the heat exchanger 12, in which it is preheated to a temperature between approximately 70° C. and 95° C., and more preferably between 88° C. and 92° C., or approximately 90° C. In the event the ambient inlet temperature is lower than 15-20 C, a preheat section may be incorporated.

The system provides a flow path operable in a continuous and/or batch manner from the inlet 10 to the outlets 17, 18. The flow path comprises components and pipes configured to maintain the fluid at the prescribed pressure and temperatures. In the exemplary embodiment, food-grade stainless steel piping is used in the system, from the inlet to the outlets, including the heating section. The choice of metal used in the materials throughout the system will be based on the requirements which best suit the particular application, but typically will be a high temperature alloy. This permits ease of installation with typical apparatus without creating a metal mismatch that could produce corrosion of the metal, due perhaps to chemical or electrochemical reactions within the system.

In another embodiment, variable speed pumps can be used to achieve a desired pressure in the system. For example, a variable speed pump can be used proximate to the inlet of the system 30 to achieve a desired inlet pressure. In addition, a variable speed pump can be placed proximate to an outlet of the system and operated in association with the inlet pressure to achieve a desired outlet pressure, but not create an internal pressure upset.

Figure 5:
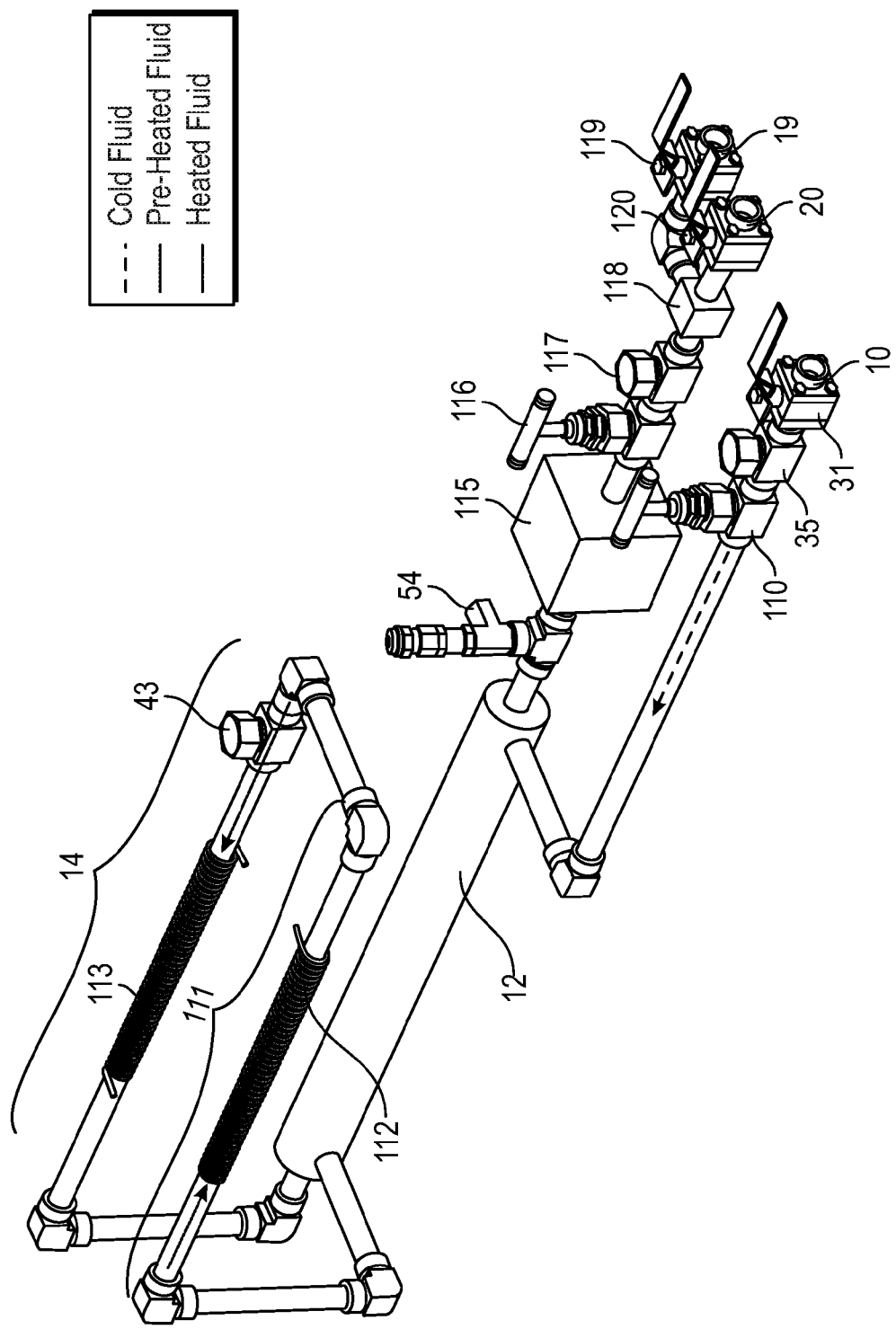
FIG. 5 is a perspective view of a fifth embodiment of a fluid sterilization assembly in accordance with the present invention illustrating an arrangement of valves.
Figure 8:
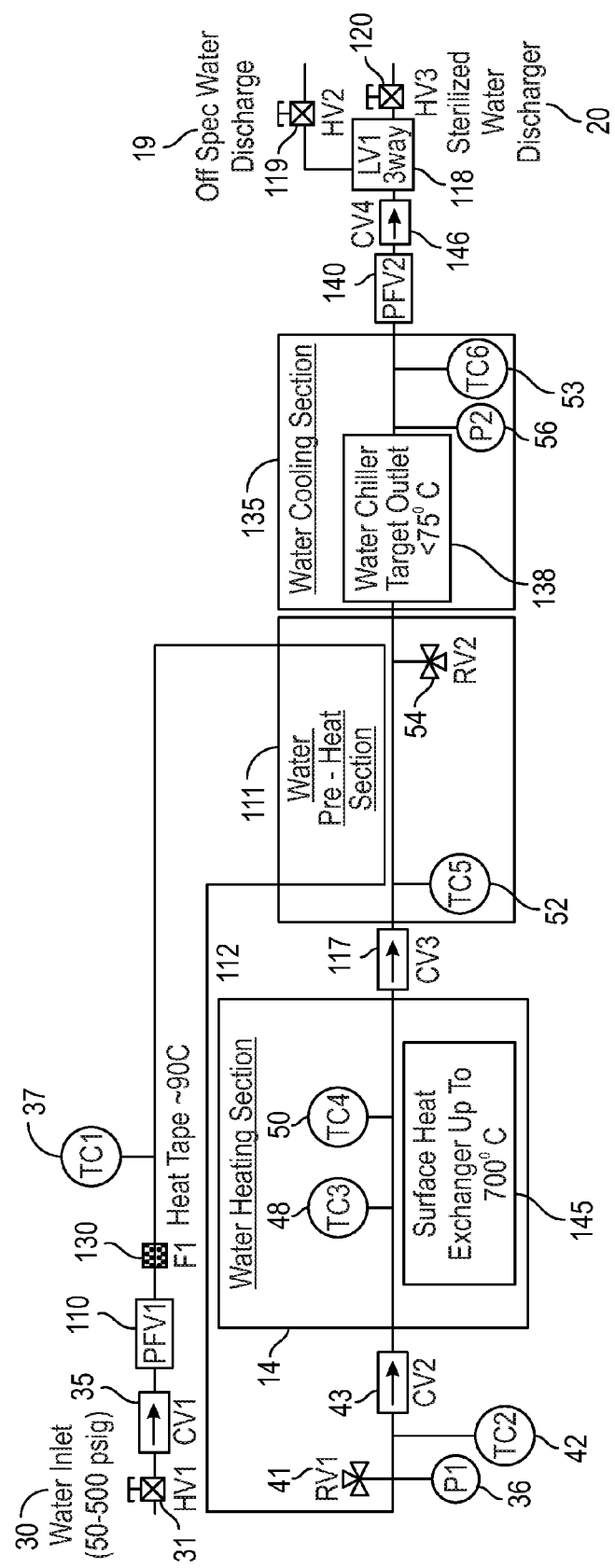
FIG. 8 is a simplified block diagram of an eighth embodiment of a fluid sterilization assembly in accordance with the present invention, incorporating a pre-heating section as well as a cooling section.

In another embodiment, best seen in FIG. 5, a heating element 112 is used to pre-heat the fluid to an even greater temperature after it leaves the heat exchanger 12. After passing through this first heating element 112 (e.g., tape heaters) in the pre-heating section 111, the fluid then flows into the heating section 14 and through the heating apparatus therein 113, to be brought up to its desired temperature for sterilization. As shown in FIG. 8, heater tape is used as the pre-heating element 112 in this embodiment, although other heating apparatus may be used, similar to the primary heating section 14 as discussed below. This pre-heating section 111 heats the fluid to a temperature between approximately 90° C. and 120° C., as measured by a second thermocouple (TC2) 42 disposed along the flow path between the heat exchanger 12 and the heating section 14. Other embodiments are envisioned, however, in which fluid passes directly from the heat exchanger 12 to the heating section 14, or even directly from the inlet 30 to the heating section 14, obviating a pre-heating section 111.

A relief valve (RV1) 41 is disposed along the flow path between the heat exchanger 12 and the heating section 14 so as to release fluid from the flow path if the pressure in the flow path exceeds a set cracking pressure (e.g., 500 psig). The actuation of a relief valve diverts fluid out of the flow path so that the pressure in the flow path will stop rising or decrease, in order to protect the system from damage or failure from excessive pressure. If actuated, the relief valves may divert excess fluid back to the system through an auxiliary flow path, or may divert excess fluid out of the system.

The heating elements are configured to bring the fluid up to the desired temperature quickly and accurately. In the exemplary embodiment, shown in FIG. 2, the heating section 14 utilizes immersion fluid heaters 47, 49, and 51, e.g., 1000-watt, as the primary heating element. Other embodiments described herein may use inductive heat exchangers 132 (FIG. 6), surface heat exchangers 145 (FIG. 8), or propane heaters 160 (FIGS. 11, 19, 24, and 25). However, other heating apparatus may be used, singly or in combination, without departing from the scope of the invention, such as tape heaters, heating rods, direct flame (e.g., using natural gas, propane, firewood or other fuels), immersion heaters, graphene (e.g., as a conductor or to administer direct heat or both), microwave, solar heaters (e.g. lenses or mirrors to concentrate heat energy), or heat from combined heat and power generators.

In addition, systems in accordance with the invention can be integrated into other mechanical structures, utilizing heat sources available therein to provide a heat source for the heating section. For example, the heating section can utilize heated components of a motorized vehicle or generator (e.g., the engine block or tailpipe) as a surface heater, so long as the desired heat can be achieved. In an exemplary embodiment, the heating section can include a flow path incorporated into a manifold integrated with heated components of a motor component such as a generator or vehicle (e.g., the engine block or tailpipe), in which the controller can manage flow rate through the heating section to maintain fluid at a prescribed temperature and pressure for a prescribed duration (e.g., dwell time) to sterilize the fluid. Notably, in this embodiment, temperature and pressure within the heating section can be monitored and sterilization controlled by fluid pressure and flow, throughout operation, while integrating the temperature of the heat supply that is dependent on operation of the motorized component.

With continued reference to FIG. 5, upon exit from the heat exchanger 12, pre-heated fluid is released into the heating section 14 by way of a second check valve (CV2) 43. Fluid is heated to between approximately 135° C. to 240° C., measured by thermocouples (TC3, TC4, etc.) 48, 50, 52, disposed in the heating section 14. The dwell time of fluid at 240° C. is approximately 1 second or less, although the dwell time can be altered as needed to sterilize fluid under different process variables.

In the exemplary embodiment, fluid is not allowed to change out of liquid state. By means of high-pressure containment, the fluid is allowed to reach high temperatures while still being maintained in a liquid state. The fluid does not need to be maintained in a liquid state, however, especially in embodiments that are not designed with high-pressure flow paths. The system is configured to heat the fluid at corresponding pressure levels to achieve effective sterilization. More particularly, the system can reach desired levels to sterilize bacteria, viruses, and prions, among other infective agents and organic pollutants. Furthermore, above a prescribed temperature, the system can break down organic molecules.

Another embodiment is envisioned in which a distillation component is disposed along the flow path, additionally or alternatively to a heating section 14. One example of such a distillation component could be a vacuum chamber, which would be evacuated prior to fluid entering the chamber, in which fluid vaporizes when it enters the low pressure zone in the chamber. This vaporized fluid would be collected as distillate at a condenser before continuing in the system. Additionally, this distillation component can be heated to sufficiently high temperatures as in a heating section 14, in order to function both as a distillation component and as a sterilization component.

The immersion water heaters 47, 49, and 51, depicted in the embodiment in FIG. 2 are designed to sufficiently fill the volume of the flow path in close proximity with the inner wall of the pipe(s) that define flow path through the heating section (heaters 47, 49, and 51), in order to provide adequate surface area for the fluid to maintain the desired contact with the surface of the heaters 47, 49, and 51, to ensure that the fluid is sufficiently heated while guarding against overheating of the heaters. For example, in an exemplary embodiment, the flow over the surface of the immersion heater can match the current to the heater or the heater will over heat if the control is set to the exit temperature of the water, but the flow is low and not removing adequate heat from the heater. One method of controlling this is to provide thermocouples on the immersion heaters to ensure that they do not overheat if the water flow drops or is reduced.

More particularly, the immersion heaters may have an elongated, cylindrical shape, wherein the heaters are oriented in axial alignment with the cylindrical pipes that define the flow path through the heating section. In this manner, the system optimizes energy transfer between the heater(s) and the fluid. The flow path in the heating section 14 can incorporate various means of increasing the efficiency of the heating element 12 as may be required by a particular embodiment. For example, turbulence generators such as, baffles or turbulators, may be disposed in the heating section 14 flow path to break the boundary layer of the fluid's otherwise laminar flow, or to increase the fluid's surface area that is in direct contact with the heating element 12. As another example, an internal turbulator running the length of the heating section 14 flow path may itself be heated as an immersion heater or as an inductive heat exchanger. Furthermore, the dimensions of the heating section 14 in any particular embodiment can be altered to suit the desired output quantities. For example, the length of the heating section 14 can be decreased for a more compact or portable system embodiment, or the diameter of the flow path therein 14 can be increased for a larger and higher-capacity system embodiment. Any dimensions can be scaled up or down to attain the desired operating variables.

The heated fluid, now sterile, exits the heating section 14 and travels back to the heat exchanger 12. In the exemplary embodiment, the heat exchanger 12 is multi-piped, allowing for the compartmentalized flow of fluid entering from the inlet 30, and heated fluid entering from the heating section 14. The proximity of the unheated fluid entering the heat exchanger 12 from the inlet 30 aids the process of cooling the heated fluid entering from the heating section 14, but the compartmentalization prevents any possible recontamination. In other embodiments, other means of heat transfer and heat exchanger design can be used without departing from the invention. For example, plate-based heat exchangers or phase-change heat exchangers may be used, singularly or in combination, instead of or in addition to tubular heat exchangers.

Figure 7:
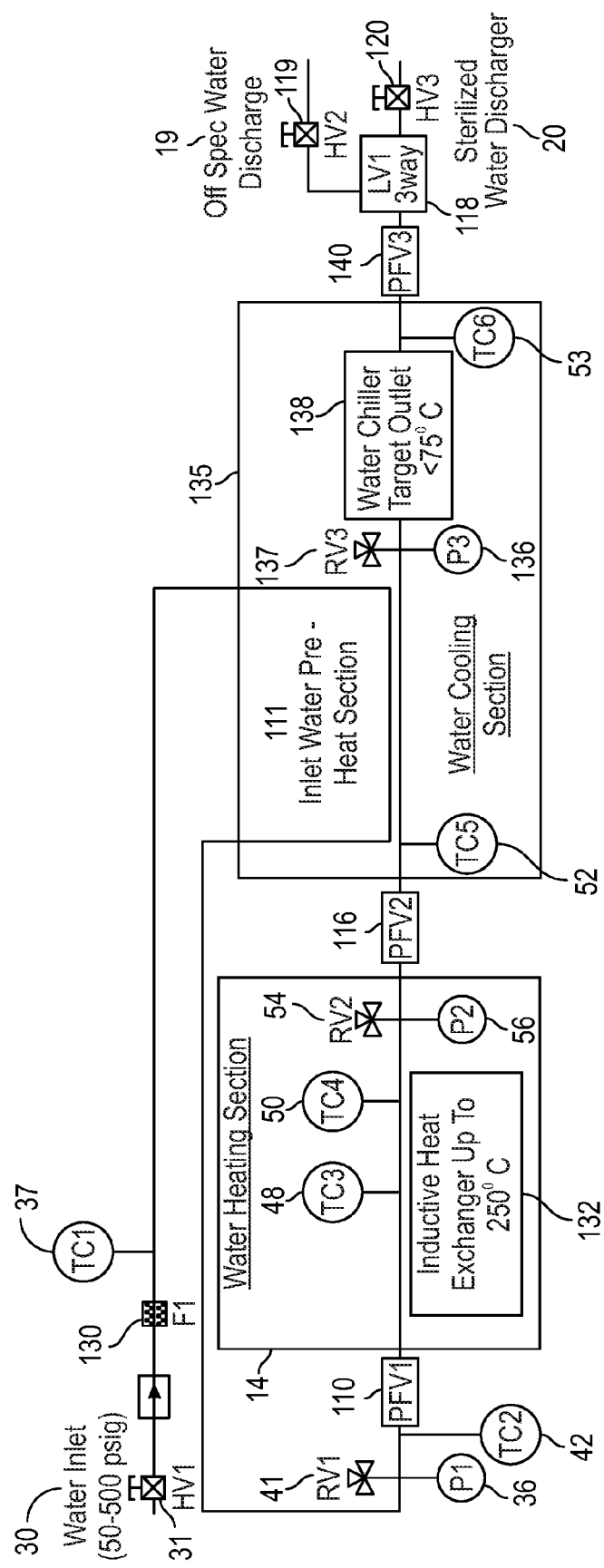
FIG. 7 is a simplified block diagram of a seventh embodiment of a fluid sterilization assembly in accordance with the present invention, incorporating a cooling section and an alternate possible arrangement of valves and sensors.

In this exemplary embodiment, the temperature of the sterile fluid is reduced to approximately 70° C. after passing through the heat exchanger 12. Another embodiment, seen in FIG. 6 and FIG. 7, incorporates a cooling section 135, comprising fluid cooling apparatus 138, to further reduce the temperature of the sterile fluid before exiting the system. The fluid is passed through another relief valve (RV2) 54 (FIG. 2) and a stepper motor proportional flow valve (SMPFV1) 57, before being directed through either a latch valve (LV2) 58 for off-spec discharge 19, or a latch valve (LV1) 60 for sterile fluid discharge 20 to exit the system. Alternatively or additionally, one three-way valve 118 (FIG. 6) could be used to direct fluid to either the off-spec discharge 19 or sterilized fluid discharge 20 flow path. The off-spec discharge 19 may be directed to exit the system, or may be directed back into the system for re-sterilization.

Figure 9:
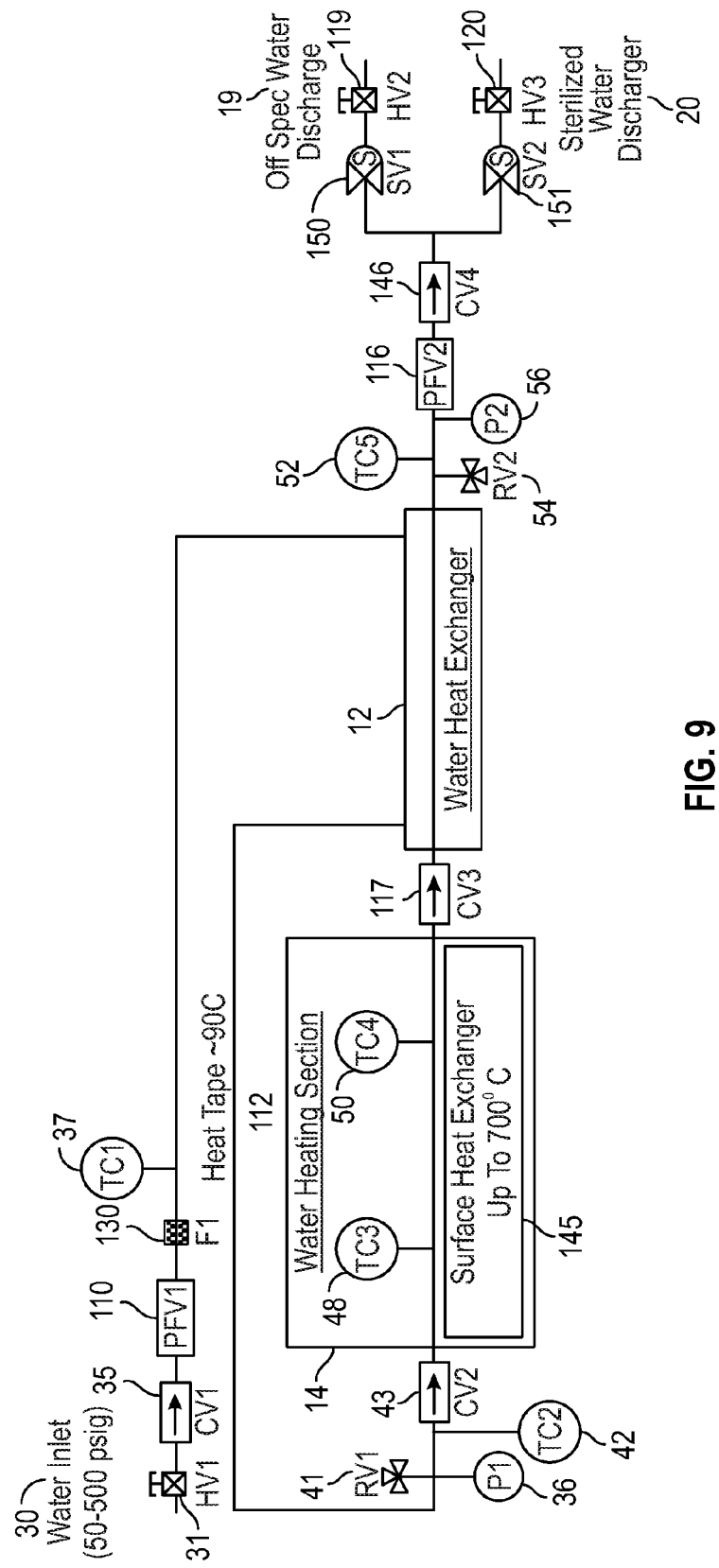
FIG. 9 is a simplified block diagram of a ninth embodiment of a fluid sterilization assembly in accordance with the present invention, incorporating a surface heat exchanger as a heating element.
Figure 10:
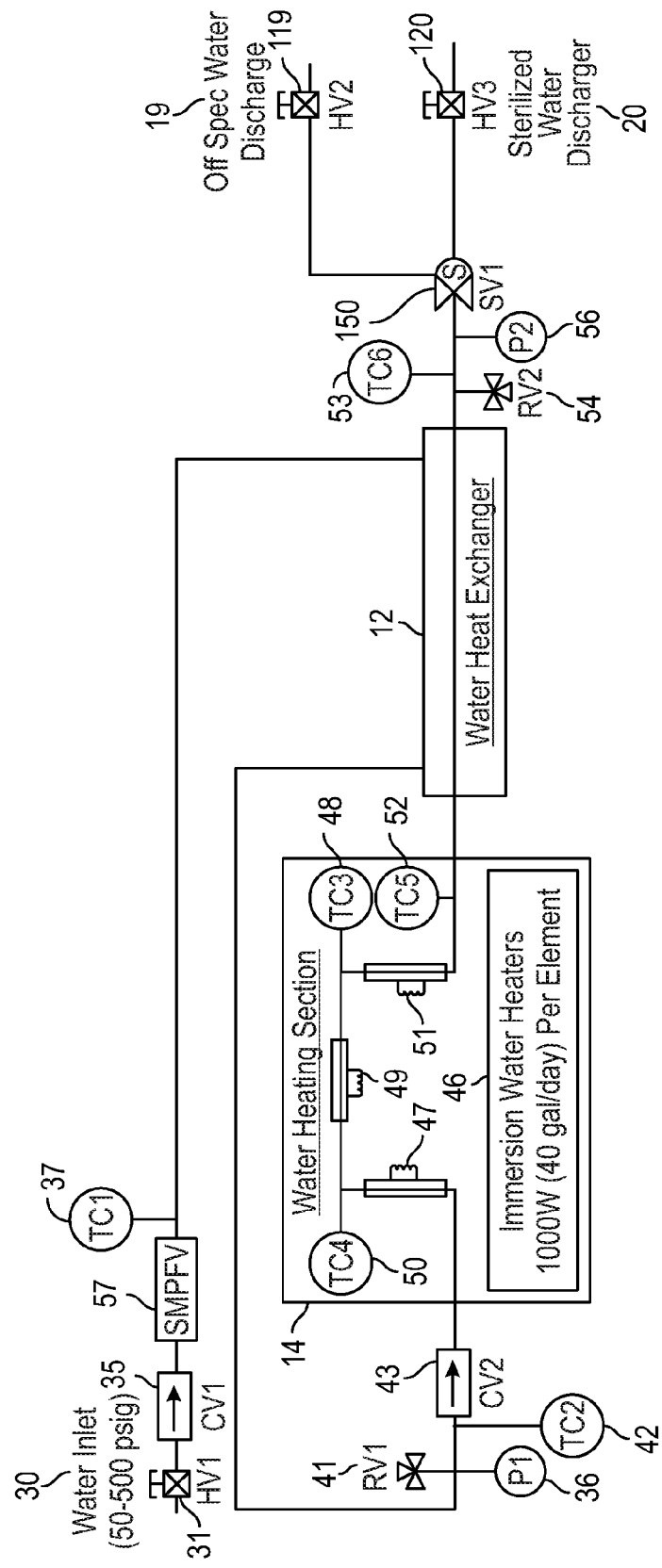
FIG. 10 is a simplified block diagram of a tenth embodiment of a fluid sterilization assembly in accordance with the present invention, incorporating immersion heat exchangers as heating apparatus.

Although the exemplary embodiment has been described as utilizing a pump 34 to ensure adequate pressure at the inlet 30, the system can be used without pumps, as seen in FIG. 9 and FIG. 10 wherein the fluid is introduced via any of several pressure systems, i.e., gravity feed from storage tower, or elevated reservoir. When fluid reaches the prescribed sterilization temperature (e.g., 250° C.), as read by TC3 48 and TC4 50, a solenoid valve (SV1) 150 for off-spec discharge 19 is opened, and the inlet 30 is opened at the first proportional flow valve (PFV1) 110. Pressure is controlled by adjustments to PFV1 110 and the second proportional flow valve (PFV2) 116. This creates a steady flow of fluid from inlet 30 to discharge 19. Once a steady flow of fluid is established for a prescribed period of time in the heating section (e.g., dwell time) in order to ensure complete sterilization (e.g., 5 seconds), without significant temperature loss (e.g., at least 240° C. maintained), as monitored by TC3 and TC4, then SV1 150 for off-spec discharge 19 is closed and a second solenoid valve (SV2) 151 for sterile fluid discharge 20 is opened. Sterile fluid is then being produced, taken in at the inlet 30 through a HV1 31, CV1 35, and PFV1 110, exiting through SV2 151 Although the embodiments herein are described in detail with reference to continuous operation or to a steady flow of fluid, other embodiments in accordance with the invention can be operated in a pulse or batch mode. For example, a controller 180 could be programmed to produce sterilized fluid for a given volume (e.g. 100 gallons) or a given duration (e.g. 1 hour) and then shut off the system. As another example, a manual operator could open the requisite valves to allow a certain volume of fluid into the heating section 14, then close the requisite valves for the desired dwell time to sterilize the volume of fluid in the heating section 14, and finally open the requisite valves to direct that volume of fluid to the sterile fluid discharge 20.

Figure 21:
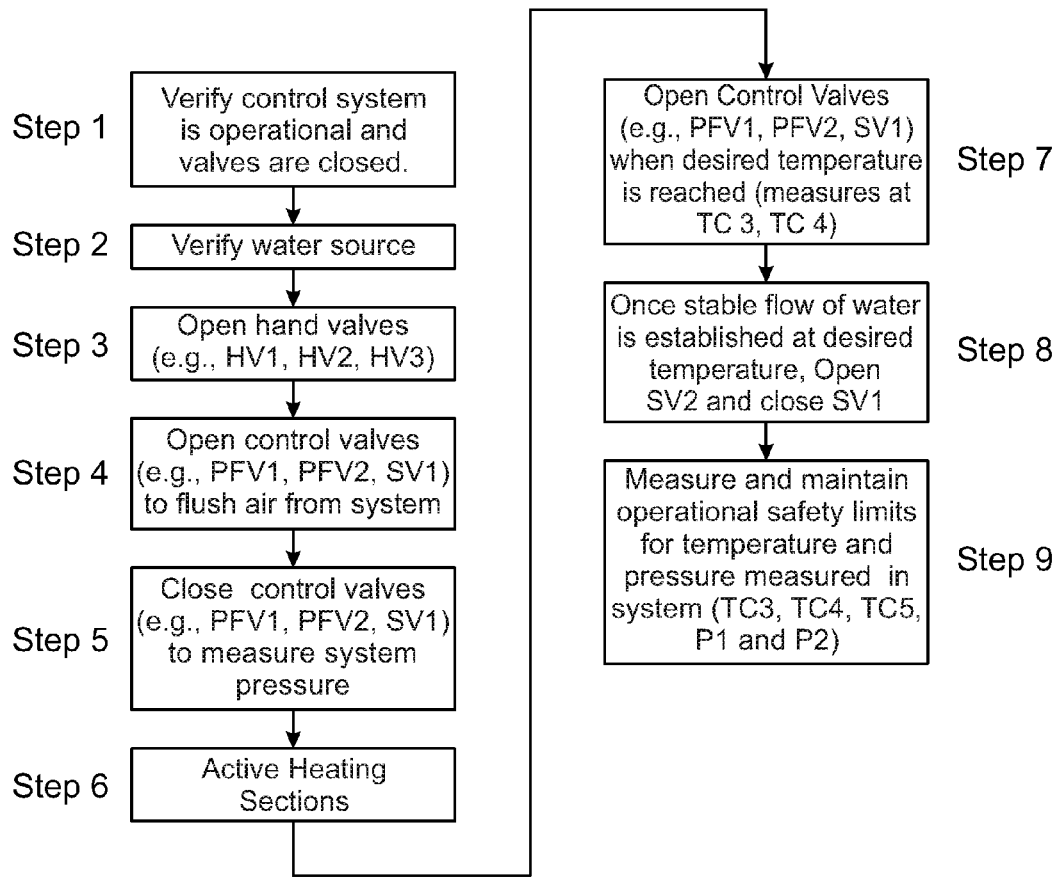
FIG. 21 is a simplified block diagram of system operation in accordance with the invention, e.g., with reference to the assembly of FIG. 9.

With reference now to FIG. 21, an exemplary sequence of operation of a system (e.g., system (FIG. 9)) in accordance with the invention is discussed. First, in the exemplary embodiment, the operator verifies the system is operational, as discussed in detail below, and all valves are closed. Next, verified the water source is attached to deliver water to the system. Step 3, the terminal valves can now be opened (e.g., HV1 HV2 HV3). Step 4, the control valves (e.g., PFV1, PFV2, SV1) are now opened to allow full flow through the assembly to flush out all air from the flow path. Step 5, close the control valves (e.g., PFV1, PFV2, SV1). Now fluid will be confined within the flow path of the system, free of air trapped therein. The controller (180) will read pressure within the system, e.g. via P1, to ensure that an initial minimum pressure (e.g., at least 50 psi) is available.

If the measured initial minimum pressure is satisfactory, then at Step 6, the controller activates the water heating sections, in the exemplary embodiment, the primary heating section is set to the prescribed sterilization temperature. Step 7, when the heating sector is the prescribed sterilization temperature, (as measured, e.g., TC3, TC4), the control valves (e.g., PFV1, PFV2, SV1) are opened to initiate flow through the system. Next, at step 8, once a stable flow fluid is established through the system for a sufficient period of time, e.g., at least 5 seconds, while maintaining a sufficient sterilization temperature, and the valve (SV1) for the off-spec discharge can be closed and the valves for sterilized fluid can be opened (SV2).

During operations, the controller 180 monitors the system to ensure operational safety is maintained and to ensure that the prescribed sterilization temperatures and pressures are maintained within prescribed tolerances. These measurements are continually monitored throughout operations throughout the system's for example, the temperature within the primary heating section is preferably between 240° C.

and 275° C. (measured at TC3 and TC4). Also, the outflow temperature (measured at TC5). Pressure within the system, as measured at P1 and P2 must be less than 500 psig. In the exemplary embodiment check browser utilized to prevent back pressure buildup in each section. Filter (F1) is used to filter out solid contaminants from entering the system. The controller monitors entry water temperature at TC1, which is preferably between 15° C. and 20° C.

Figure 22:
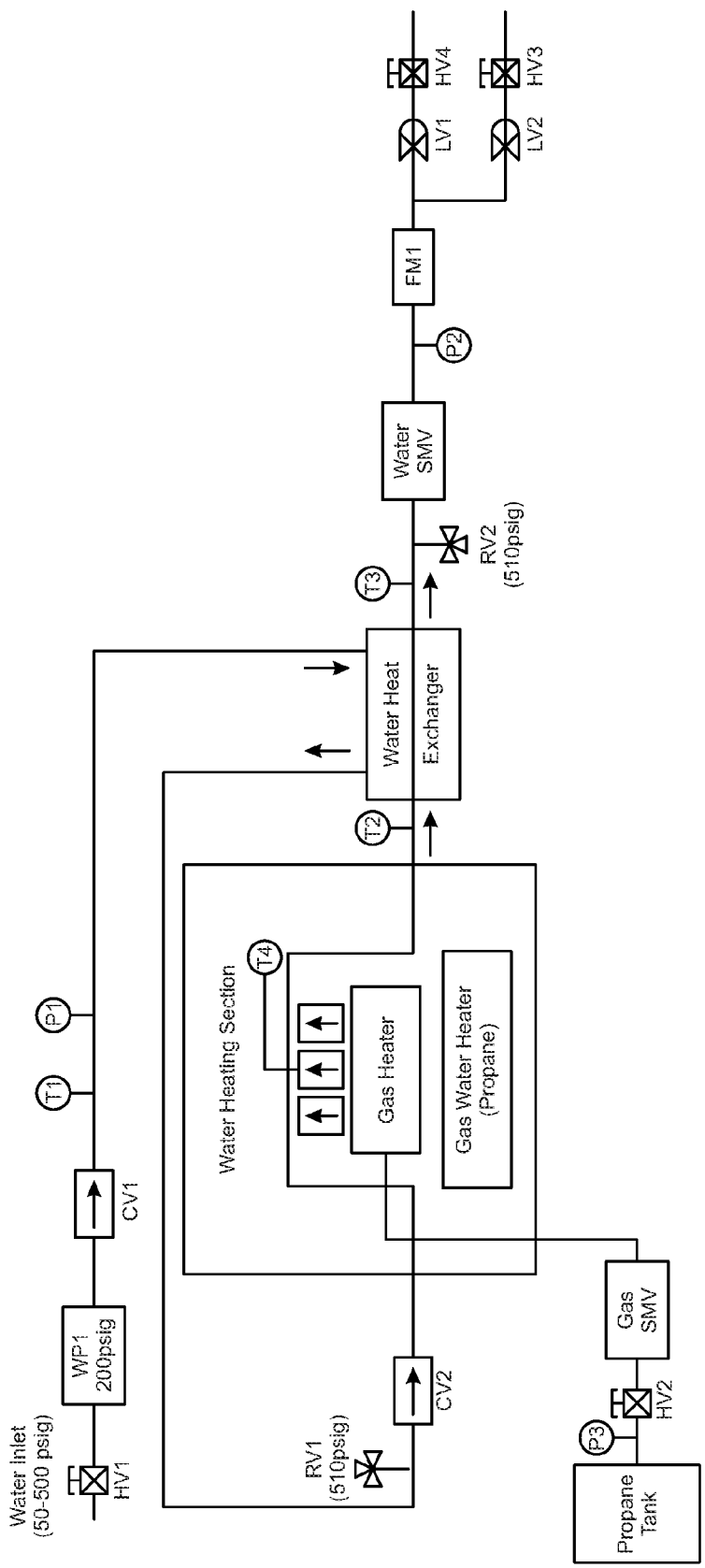
FIG. 22 is a perspective view of another embodiment of a fluid sterilization assembly in accordance with the present invention, incorporating a gas heater.
Figure 26:
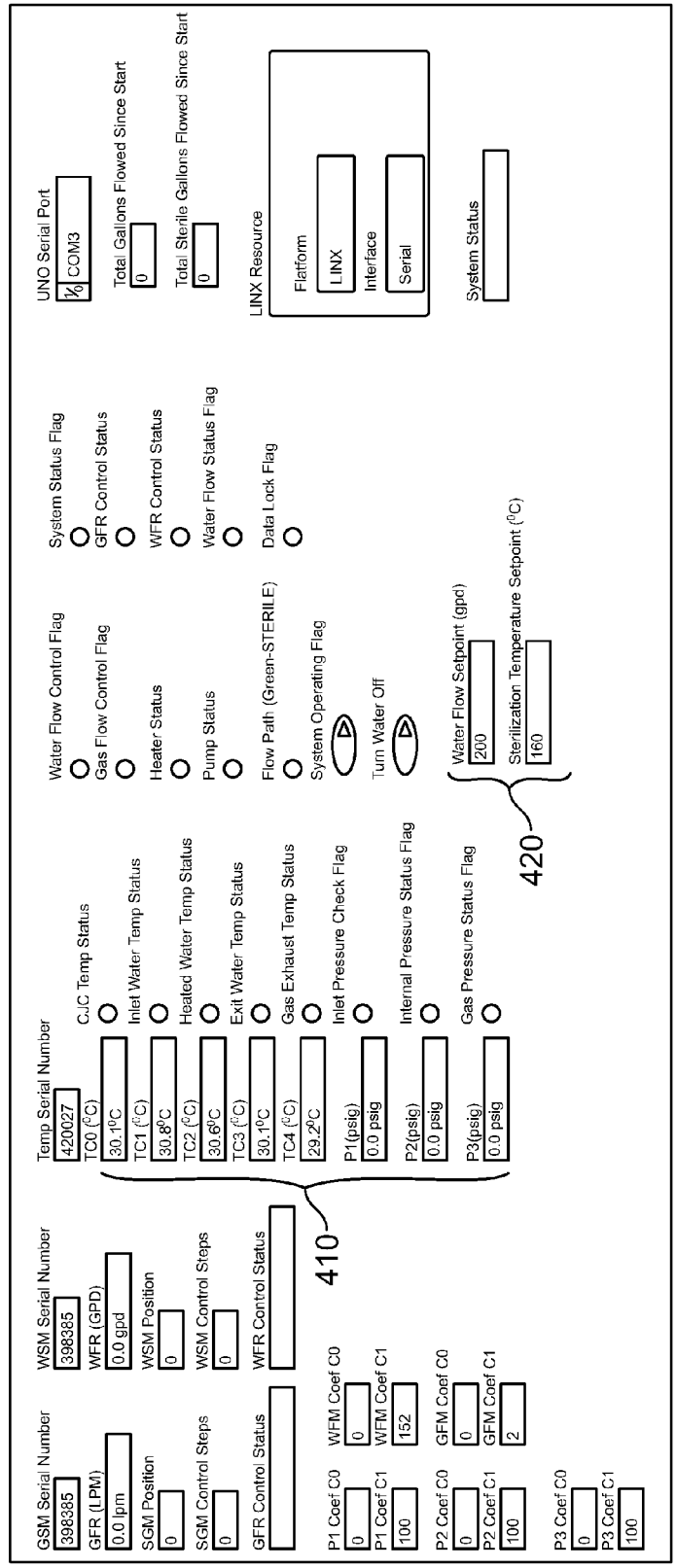
FIG. 26 is an exemplary screenshot of a status monitoring screen of the fluid sterilization assembly of FIG. 22.
Figure 27:
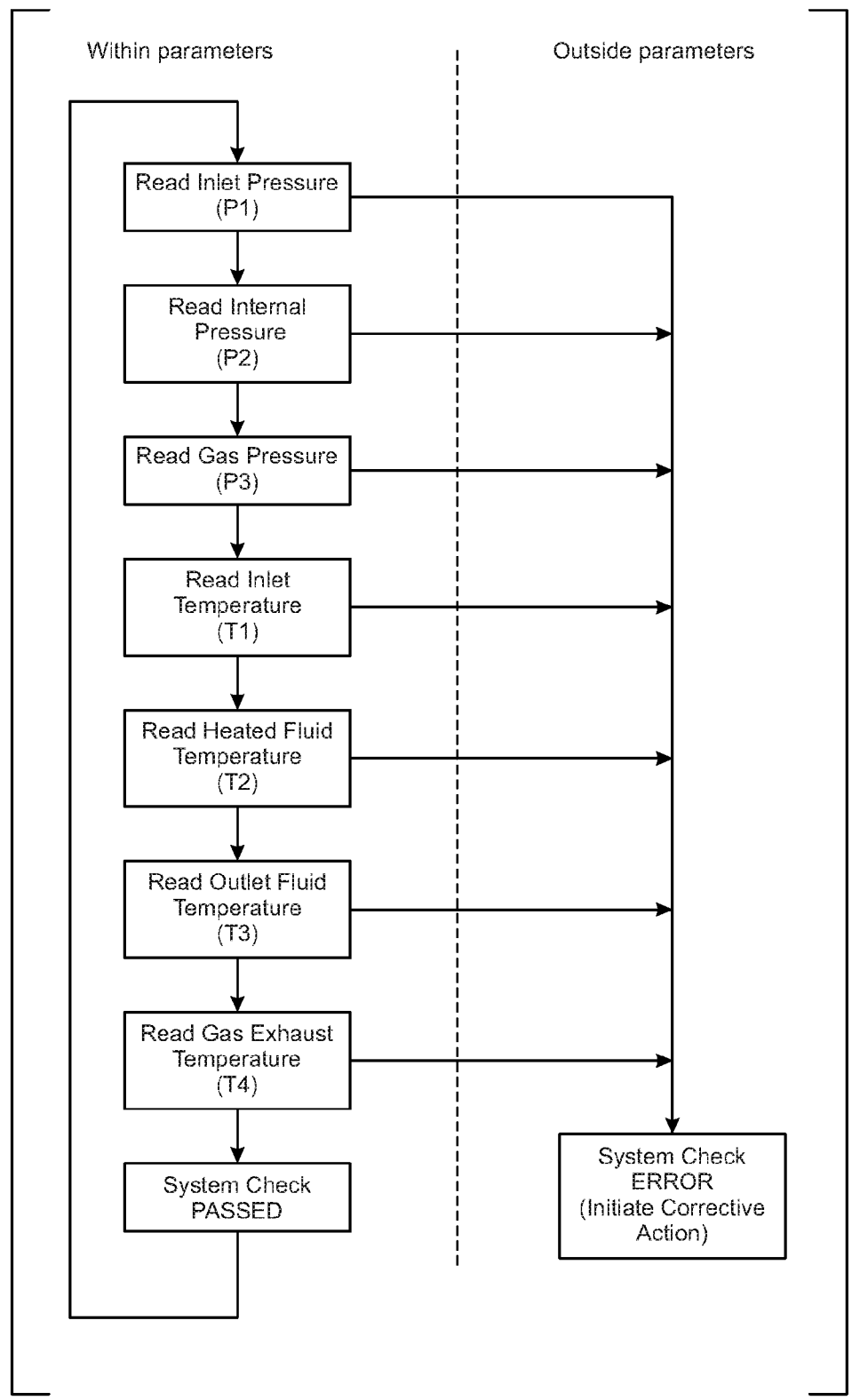
FIG. 27 is a simplified flow chart of system status operations of the fluid sterilization assembly of FIG. 22.

FIG. 26 depicts a screenshot 400 from the controller 180 depicting a status monitor for the system. The controller monitors the sensors and controls the valves, heating elements and other feature of the system. During use, the controller ensures that the system operates within prescribed ranges for pressure and temperature to achieve the desired level of sterilization without need of maintaining a fixed temperature or a fixed pressure within any portion of the system, including the heating section. This further ensure safe operation of the system. In the exemplary embodiment, the measurements 410 depicted in screenshot 400 are received from sensors (TC1, TC2, TC3, TC4, P1, P2, P3 of FIG. 22). The controller further enables the operator to designate the sterilization set point and water flow set point (420). The controller continually updates its measurements and controls, e.g., as shown in FIG. 27.

Figure 13:
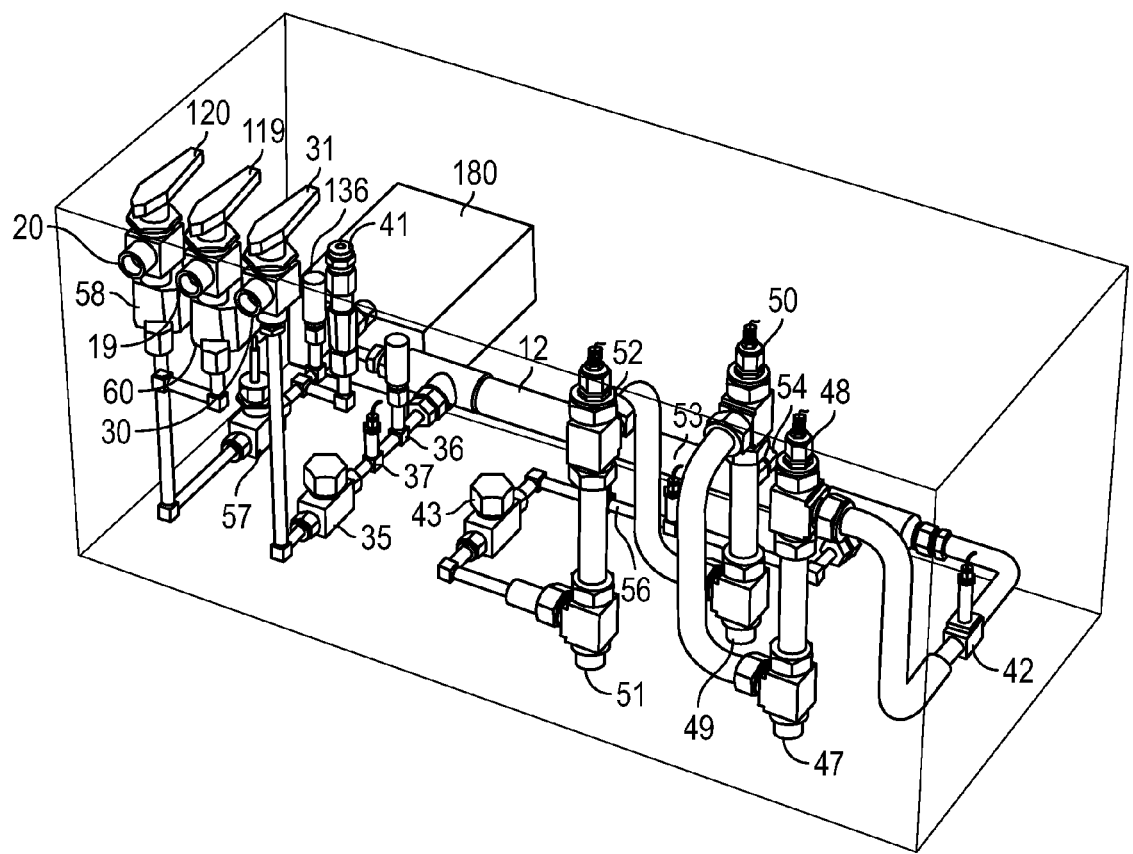
FIG. 13 is a perspective view of a thirteenth embodiment of a fluid sterilization assembly in accordance with the present invention, incorporating a controller to read sensors and actuate valves.
Figure 14:
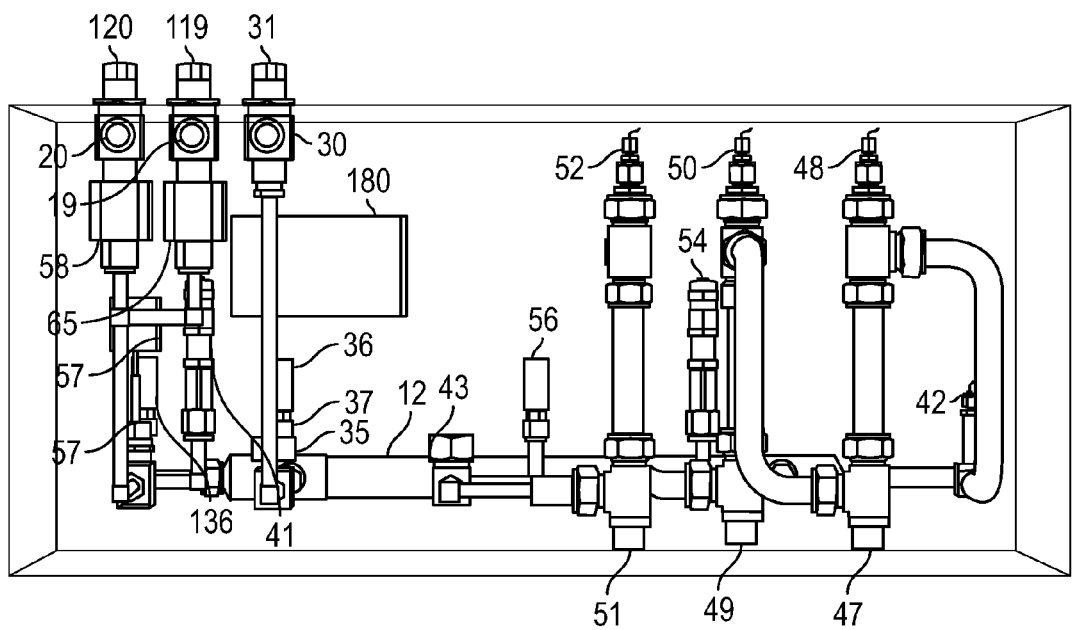
FIG. 14 is a front view of the fluid sterilization assembly depicted in FIG. 13.
Figure 15:
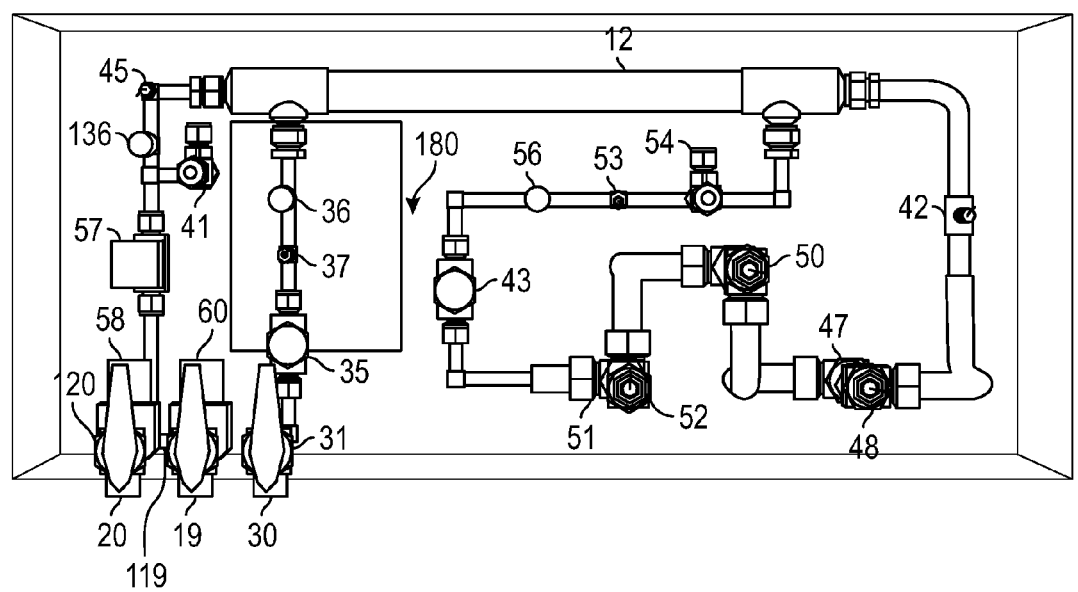
FIG. 15 is a top view of the fluid sterilization assembly depicted in FIG. 13.
Figure 16:
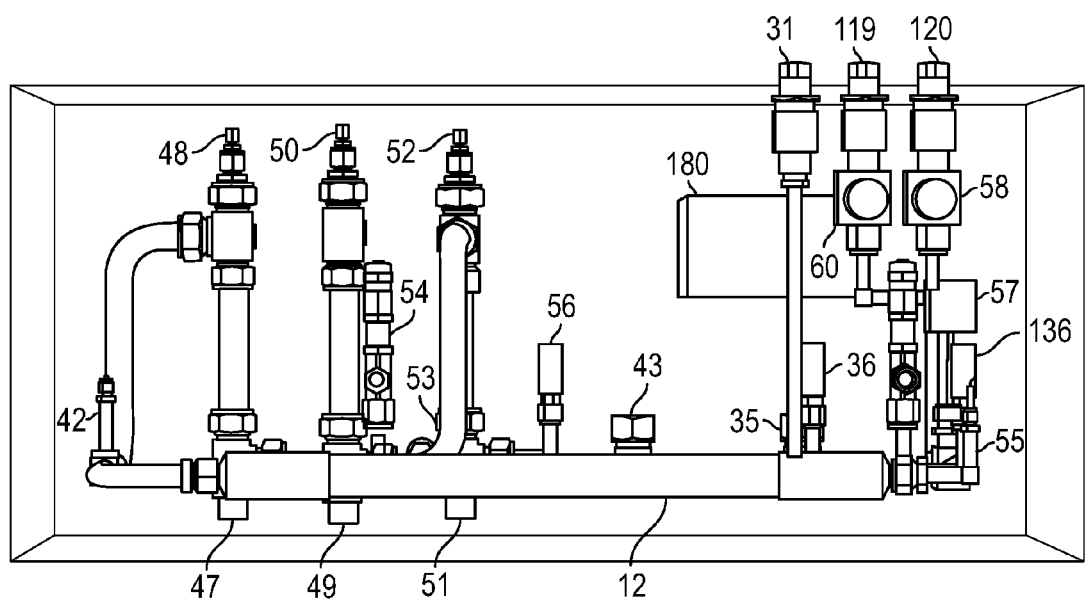
FIG. 16 is a rear view of the fluid sterilization assembly depicted in FIG. 13.
Figure 17:
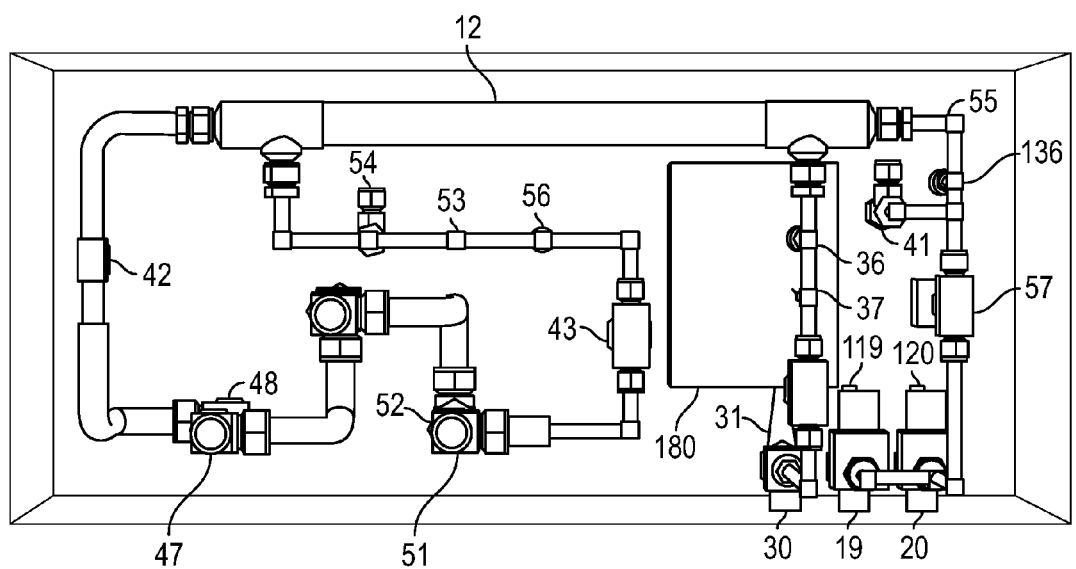
FIG. 17 is a bottom view of the fluid sterilization assembly depicted in FIG. 13.
Figure 18:
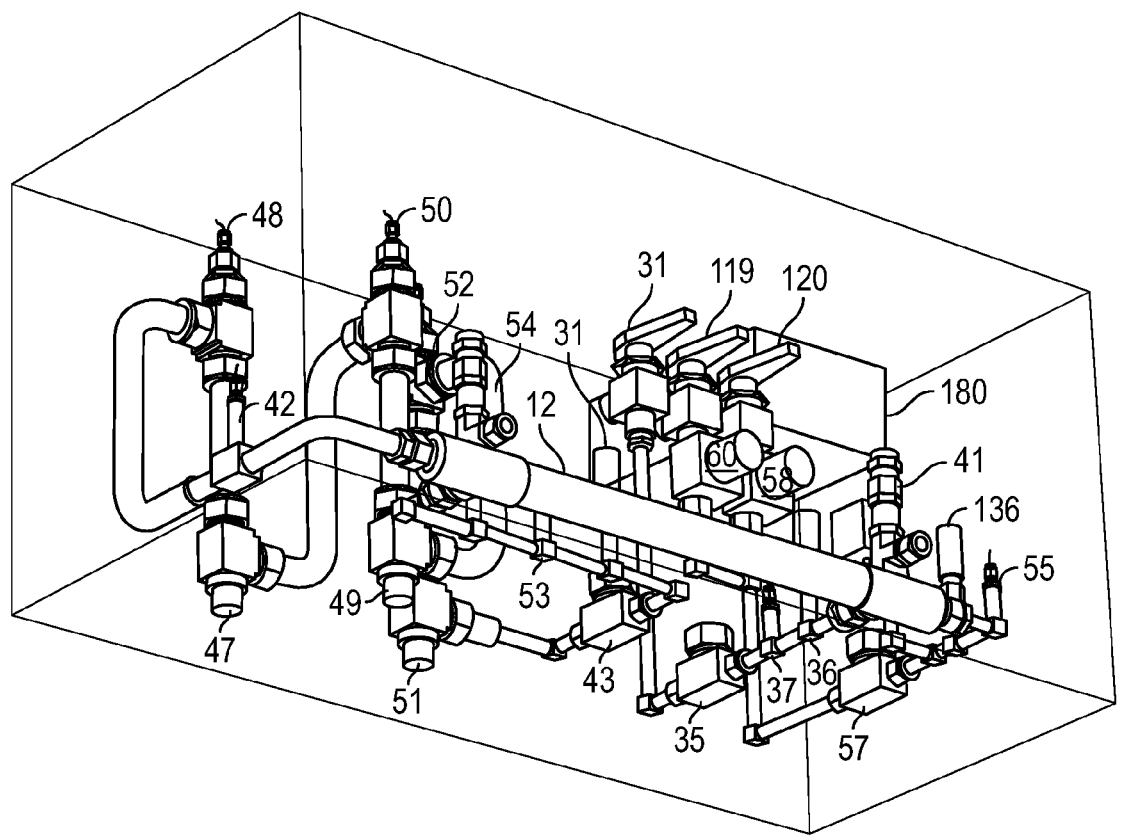
FIG. 18 is a different perspective view of the fluid sterilization assembly depicted in FIG. 13.
Figure 19:
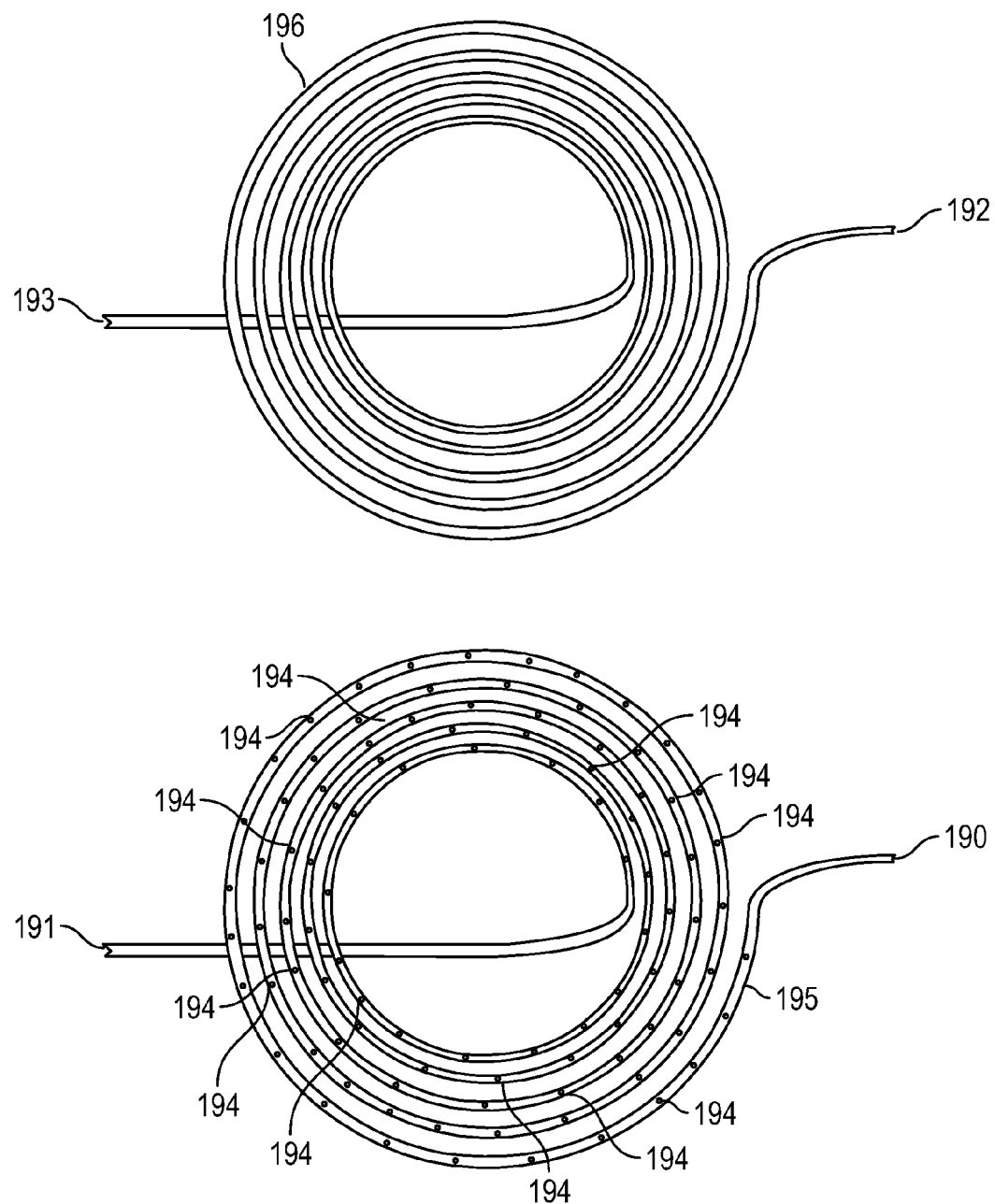
FIG. 19 is a top view of one configuration of the propane-based heater utilized in the embodiment depicted in FIG. 11.

FIG. 13 through FIG. 18 depict several views of an embodiment utilizing a controller 180. FIG. 13 shows the system from the perspective of the front upper right corner. FIG. 14 shows the system from the front, while FIG. 15 shows the system from the top. Similarly, FIG. 16 shows the system from the rear, while FIG. 17 shows the system from the bottom. Finally, FIG. 18 shows the system from the rear lower right corner. In this embodiment, the system incorporates a plurality of valves coupled to the controller 180, including valves disposed at inlet and outlet points of the heat exchanger 12 and at inlet and outlet points of the heating section 14. The valves are operated in a controlled sequence to enable effective operation of the system to include maintaining fluid within the heating section 14 for the desired duration to achieve sterilization. Thereafter, inlet and outlet ports are opened in a sequenced manner to enable the fluid to exit the heating section 14 while creating a draw received fluid from the heat exchanger 12 into the heating section 14. In this manner, the system can be operated free of pumps, while achieving the desired pressure levels due at least in part to control them sequence operation of the valves via the controller 180.

Figure 3:
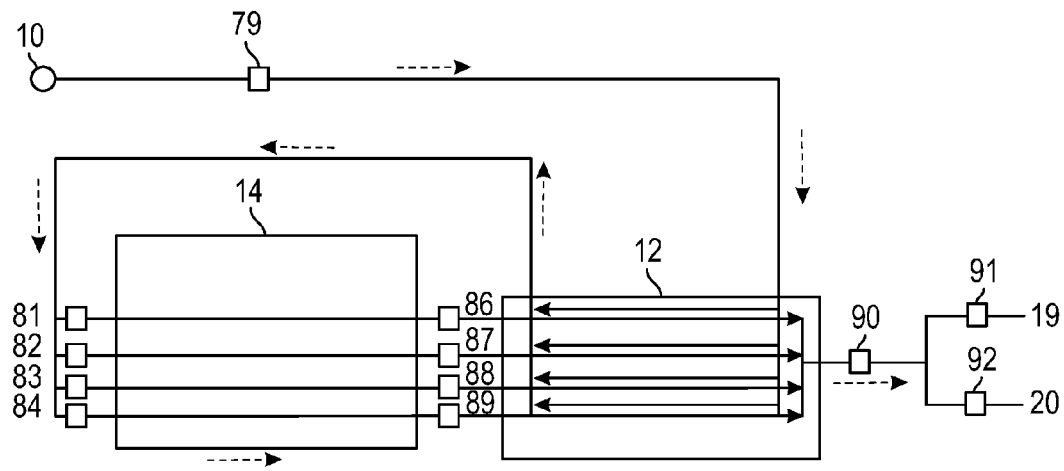
FIG. 3 is a simplified block diagram of a third embodiment of a fluid sterilization assembly in accordance with the present invention, including pipes running in parallel through the heat exchanger and the heating section.
Figure 20:
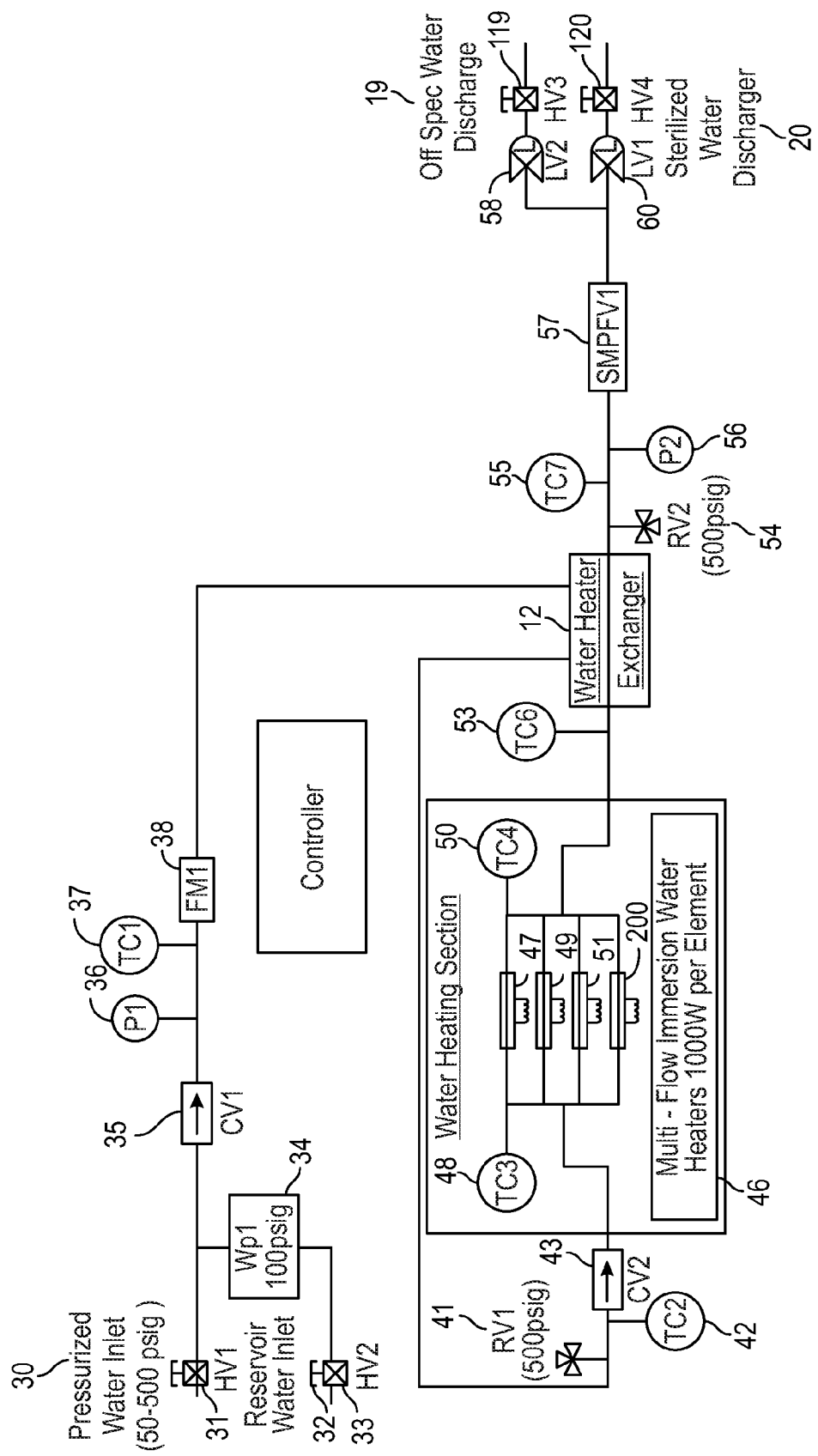
FIG. 20 is a variation on the embodiment depicted in FIG. 2 using a bifurcated immersion heater system.

With reference now to FIG. 3, a bifurcated fluid sterilization assembly, usable for sterilizing water, is shown similar to the aforementioned embodiments, further including multiple flow paths 81, 82, 83, 84, 86, 87, 88, and 89, running in parallel through the heat exchanger 12 and the heating section 14. Along each of the flow paths is disposed a plurality of valves, such that each flow path can be operated in an independent manner. Operation of each of the flow paths, however, can be sequenced such that continuous simultaneous operation can be achieved by the assembly, thereby amplifying the flow throughput of the overall system. Moreover, the controllable operation of the parallel flow paths enables users to tailor the system's output to satisfy users demand levels in real time. Other embodiments can utilize bifurcated or unbifurcated flow paths as necessary to achieve different outputs. For example, FIG. 20 depicts a variation on the embodiment in FIG. 2 using immersion heaters 47, 49, 51, and 200, disposed along bifurcated flow paths in the heating section 14.

Figure 4:
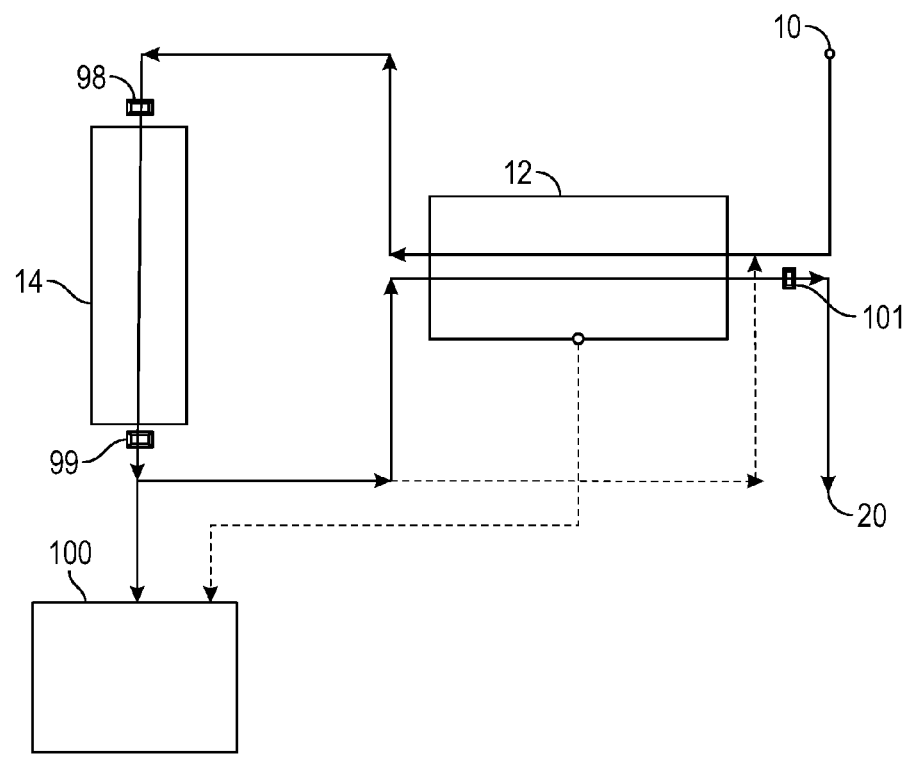
FIG. 4 is a simplified block diagram of a fourth embodiment of a fluid sterilization assembly in accordance with the present invention, incorporating an autoclave chamber using fluid.
Figure 12:
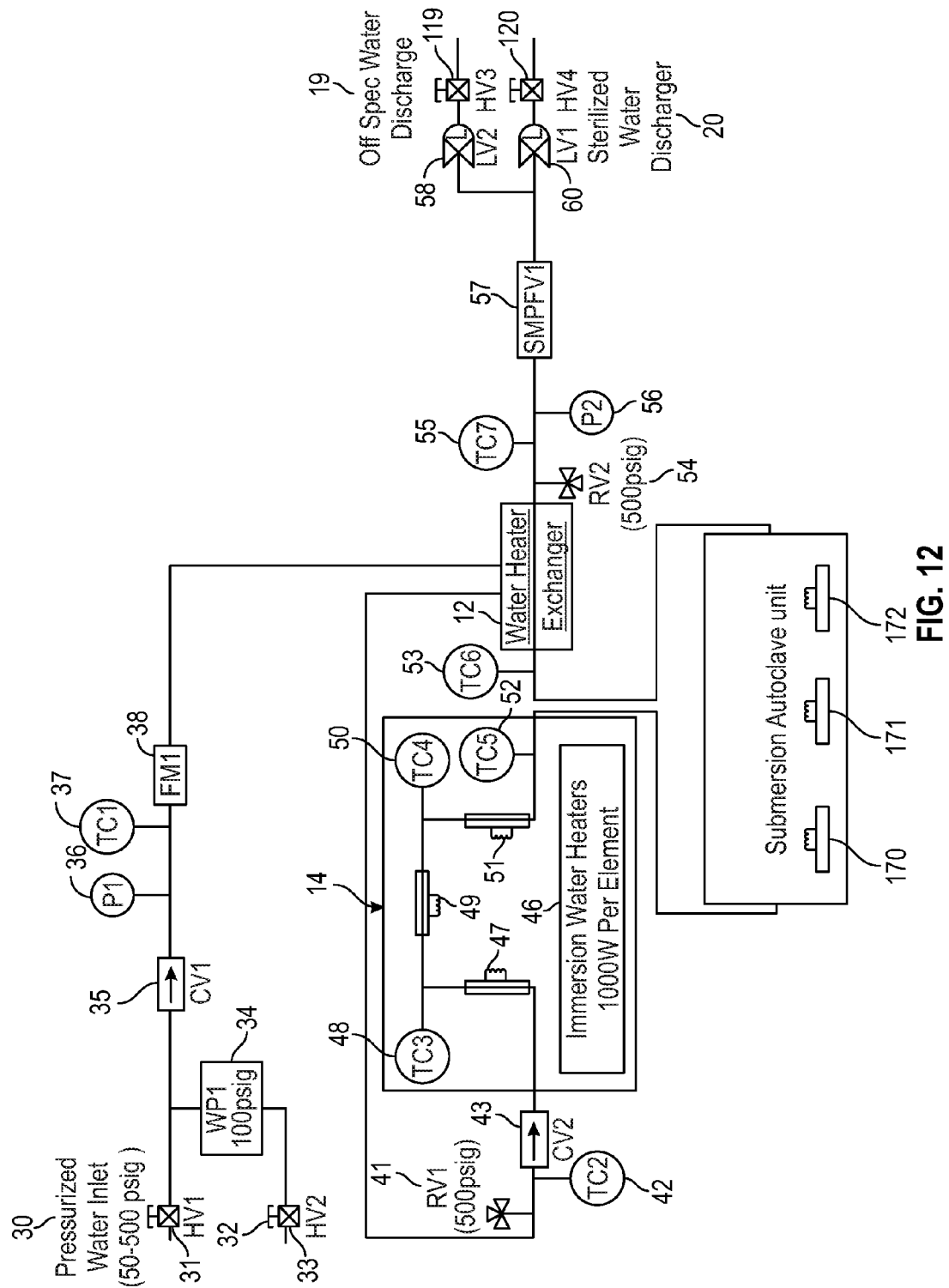
FIG. 12 is a simplified block diagram of a twelfth embodiment of a fluid sterilization assembly in accordance with the present invention, incorporating an autoclave chamber with electric immersion heaters.

With reference now to FIG. 4, the assembly can further include an autoclave chamber 100 to sterilize equipment or supplies (e.g., medical, surgical, such as drills, scalpels etc.). More particularly, the autoclave chamber 100 is configured to expose equipment to pressurized fluid maintained above thresholds for temperature and pressure for a prescribed duration (e.g., dwell time) to achieve desired levels of sterilization, while maintaining the fluid in a liquid state. The autoclave chamber 100 provides an enclosure for receiving the equipment, which can be flooded with the pressurized fluid received from the heating section 14 for sterilization. The autoclave chamber 100 is coupled to the heating section 14 of the assembly to receive pressurized fluid outflow therefrom. Additional heating apparatus, 170, 171, and 172 (FIG. 12), can be included in the autoclave unit 100 to ensure a consistent temperature of the fluid or to aid with drying of sterilized equipment.

In use, equipment is placed in the autoclave chamber 100. The chamber 100 is then pressurized, filled with pressurized fluid from the heating section 14. Preferably, the fluid is above a minimum temperature (e.g., 141° C.), and above a minimum pressure to maintain liquid state. The equipment is exposed for a prescribed duration (e.g., dwell time) to ensure sterilization. Thereafter, fluid is drained from the autoclave chamber 100, and sterile fluid cooled from the heat exchanger 12 may be directed into the chamber 100 to cool the equipment. The chamber 100 is then drained of fluid, and the sterilized equipment can be removed.

The outflow from the autoclave chamber 100 can be recirculated through the system. In the exemplary embodiment, the outflow is directed back to the heat exchanger 12 so that it can be recirculated to the heat exchanger 12 and the heating section 14. Alternatively, the outflow can be directed through an off-spec discharge 19 or, since the fluid used to sterilize the equipment in the autoclave chamber is sterile, through a sterile fluid discharge 20. With reference now to FIG. 5, a perspective view is shown of a sterilization assembly in accordance with the invention. The system can be coupled to a fluid source and electrical power and thereafter can quickly initiate operations. Notably, this assembly is compact and lightweight such that it can be transported with ease to virtually any location. In this manner, sterilized fluid can be made widely available. The embodiment depicted in FIG. 5 measures less than 1 foot in height, less than 6 feet in length, and approximately one foot in width, although even smaller assemblies are possible. Alternatively, even larger assemblies are possible with which to provide increased sterilization capabilities.

A sterilization assembly embodiment may utilize various power sources. One configuration may include lithium ion batteries or other forms of energy storage with which to operate the sterilization assembly, or at least to operate any electronic equipment therein. Solar panels may be incorporated to charge said batteries or to operate a controller 180 or other electronic equipment. Another configuration, seen in FIG. 11, incorporates thermoelectric generators (TEG1, TEG2, TEG3, and TEG4) 162, 163, 164, and 165, in the heating section 14 to recover some of the excess heat generated by the propane heating element 160 and 161 therein, and convert it to electricity to operate the assembly's electronic equipment. The assembly can include a plurality of batteries. In use, a subset of the plurality of batteries can be charging while other batteries can be powering the assembly, thereafter alternate, once the batteries are charged. The controller can be configured to manage the batteries in this manner.

Figure 11:
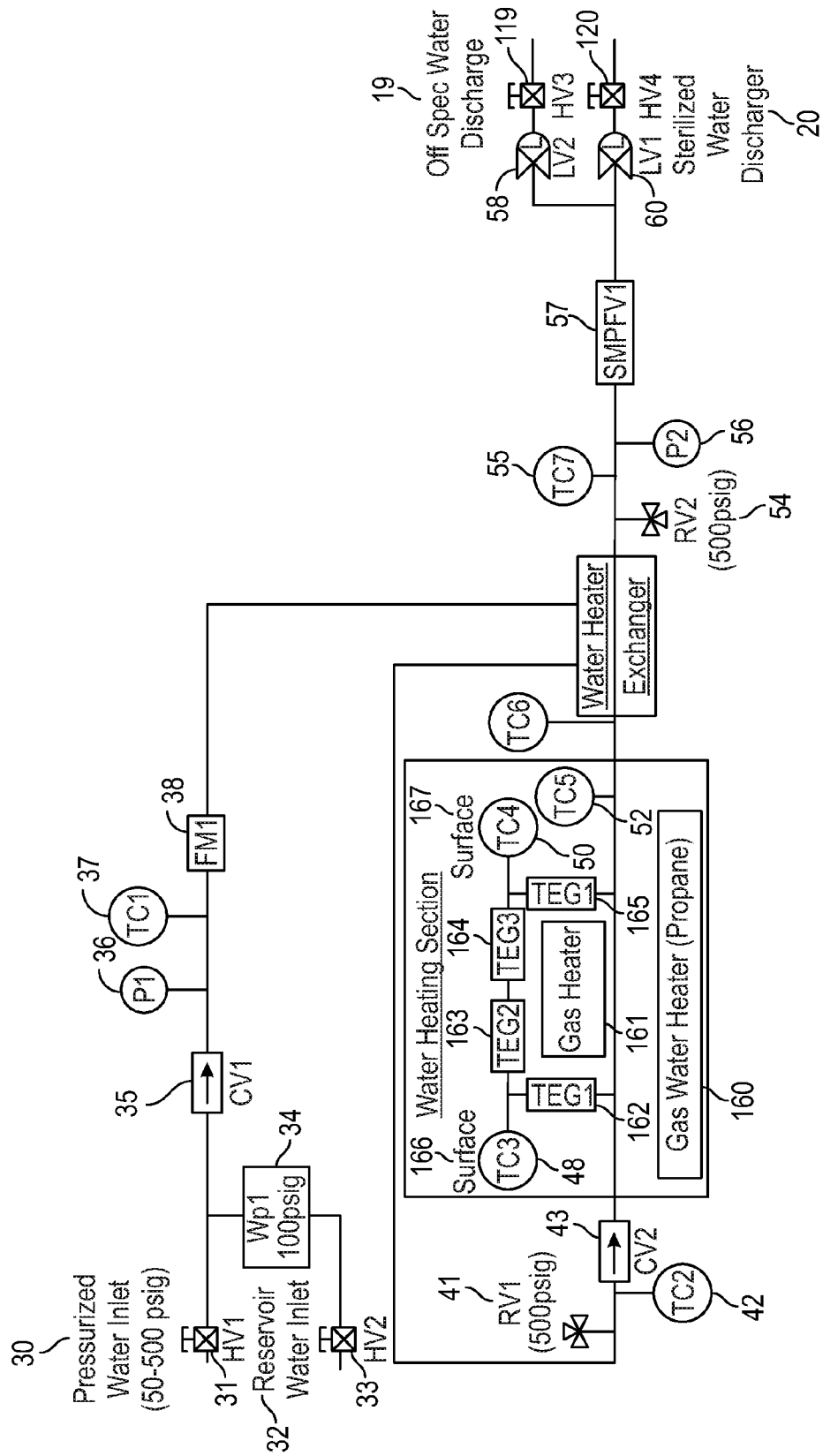
FIG. 11 is a simplified block diagram of an eleventh embodiment of a fluid sterilization assembly in accordance with the present invention, incorporating a propane-based heater and thermoelectric generators.
Figure 23:
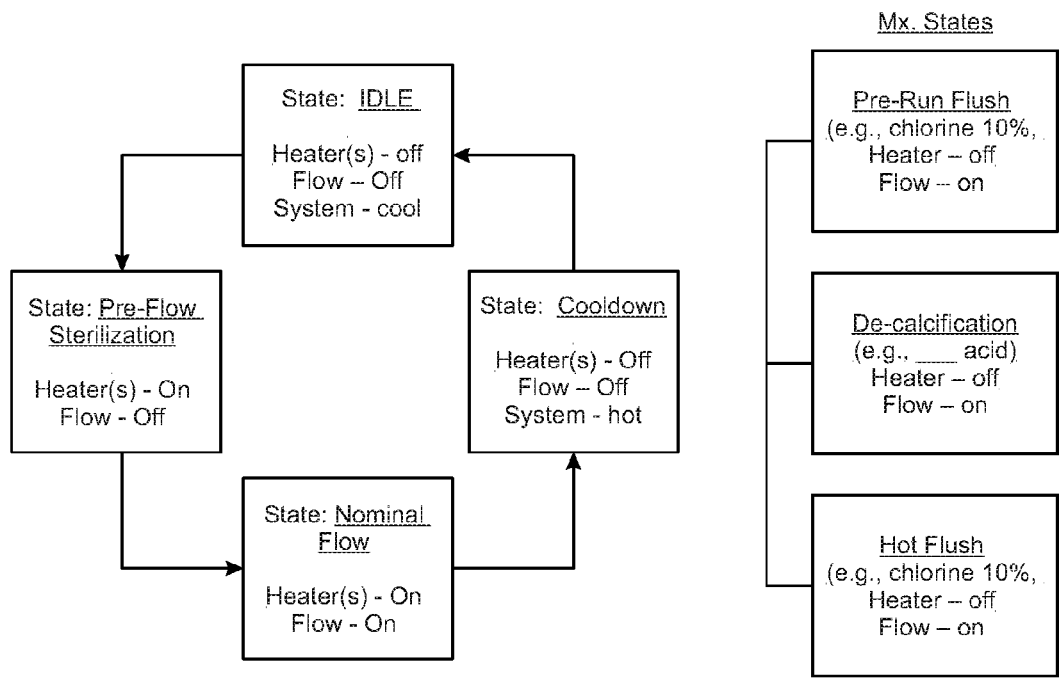
FIG. 23 is a simplified block diagram of machine states for system operation in accordance with the invention.
Figure 24:
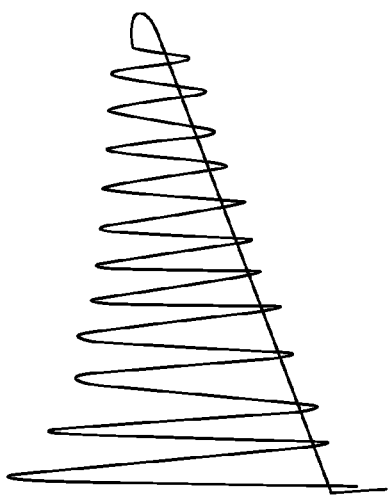
FIG. 24 is a side view of a propane-based heater that can be used in a heater assembly of a fluid sterilization assembly in accordance with the invention.
Figure 25:
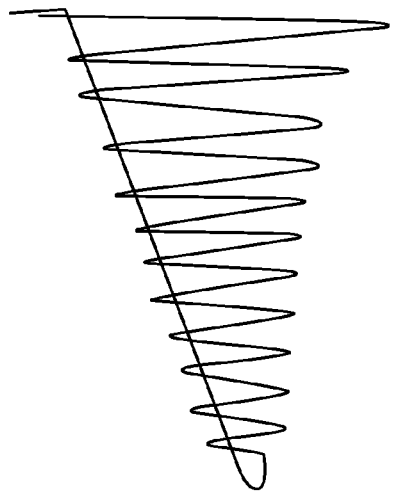
FIG. 25 is a side view of another propane-based heater that can be used in a heater assembly of a fluid sterilization assembly in accordance with the invention.

FIG. 18 depicts a more detailed diagram of the gas heater assembly 161 represented in FIG. 11, such that the fluid enters a coiled loop flow path 196 (FIG. 19), which is situated above a matching flow path for propane or other fuel 195, flowing into the coil, 190, the latter path having regularly spaced perforations 194 out of which the fuel is directed and ignited in order to heat the fluid in the upper flow path 196. See also FIG. 22 for another example of an assembly incorporating a gas heating source. FIGS. 23 and 24 depict gas heater assemblies that incorporate a coiled loop flow path configured in a frusto-conic configuration, situated above a matching flow path for propane or other fuel, the latter path having regularly spaced perforations out of which the fuel is directed and ignited in order to heat the fluid in the upper flow path.

Another embodiment is envisioned in which a sterilization system, incorporating a system controller 180, includes a means for transmitting or receiving information regarding the system. For example, a controller 180 in the system could be connected to a network to transmit sensor data to, and receive commands from, a remote operator. As another example, a controller 180 in the system may be equipped to broadcast an electromagnetic signal (e.g., radio waves) to transmit operational status, output rate, or maintenance needs (e.g., readiness, system state of health) in order to monitor the system remotely.

It should be appreciated from the foregoing that the present invention provides a system and method of fluid sterilization which incorporates a heating apparatus to heat pressurized fluid above prescribed thresholds for temperature, pressure, and duration (e.g., dwell time) to achieve desired levels of sterilization, including a heat exchanger to both (a) preheat fluid prior to entering the heating apparatus and (b) cool outflow of the heating apparatus, and in which fluid travels through the apparatus by operating valves forward and aft of the heating section in a controlled sequence to facilitate flow through the system while maintain prescribed pressure and temperature profiles. The system operates within prescribed ranges for pressure and temperature to achieve the desired level of sterilization without need of maintaining a fixed temperature or a fixed pressure within any portion of the system, including the heating section. Moreover, embodiments in accordance with the invention can be tailored for residential, business, or industrial uses, as desired.

The present invention has been described above in terms of presently preferred embodiments so that an understanding of the present invention can be conveyed. However, there are other embodiments not specifically described herein for which the present invention is applicable. Therefore, the present invention should not to be seen as limited to the forms shown, which is to be considered illustrative rather than restrictive.

What is claimed is:

1. A system for fluid sterilization, comprising:
   an inlet for operative connection to a fluid source to provide fluid along a flow path for sterilization by the system;
   a heating section in fluid communication with the inlet along the flow path, the heating section heats pressurized fluid therein above prescribed thresholds for temperature, pressure, and dwell time to achieve a desired level of sterilization;
   a heat exchanger having a first path disposed in fluid communication between the inlet and the heating section along the flow path to preheat fluid prior to entering the heating section and having a second path positioned between the heating section and a system outlet along the flow path to cool outflow of the heating section prior to exiting the outlet, wherein the first path and the second path of the heat exchanger are configured to pass heat energy therebetween; and
   a plurality of valves disposed along the flow path, including a first valve positioned on the flow path after the inlet and prior to the first path of the heat exchanger and a second valve positioned on the flow path after the first path of the heat exchanger and prior to the heating section;
   a plurality of sensors disposed along the flow path, including (a) a pressure sensor positioned on the flow path after the inlet and prior to the first path of the heat exchanger, (b) temperature sensors disposed in the heating section to measure fluid temperature therein, (c) a pressure sensor positioned on the flow path after the heating section and prior to the outlet; and (d) a temperature sensor positioned on the flow path after the heating section and prior to the outlet;
   a digital controller in operative communication with the plurality of sensors to receive measurements therefrom and in operative control of the plurality of valves to operate the valves in a controlled sequence to facilitate flow through the system while controlling to prescribed pressure and temperature profiles across prescribed ranges for pressure and temperature to achieve the desired level of sterilization without need of maintaining a fixed temperature or a fixed pressure within any portion of the system, including the heating section.

2. The system for fluid sterilization as defined in claim 1, wherein the heating section comprises immersion heaters oriented in axial alignment with the flow path through the heating section.

3. The system for fluid sterilization as defined in claim 1, wherein the heating section comprises a manifold integrated with a heated component of a motorized generator or motorized vehicle.

4. The system for fluid sterilization as defined in claim 1, wherein the plurality of valves includes:
   a third valve downstream of the heating section and upstream of the second path of the heat exchanger, and
   a fourth valve downstream of the second path of heat exchanger and upstream of the outlet.

5. The system for fluid sterilization as defined in claim 1, further comprising a cooling apparatus disposed downstream of the second path of the heat exchanger and upstream of the outlet along the flow path.

6. The system for fluid sterilization as defined in claim 1, further comprising tape heaters coupled along the flow path downstream of the first path of the heat exchanger and upstream of the heating section.

7. The system for fluid sterilization as defined in claim 1, wherein the heating section comprises a distillation component disposed along the flow path, in which fluid vaporizes when it enters a low pressure zone therein, the vaporized fluid collects as distillate at a condenser before continuing downstream along the flow path.

8. The system for fluid sterilization as defined in claim 1, wherein the heating section comprise turbulence generators to create turbulent flow of fluid therein proximate to heaters therein.

9. The system for fluid sterilization as defined in claim 1, wherein the heating section comprises a heat source selected from a group consisting of tape heaters, heating rods, direct flame, immersion heaters, graphene, microwave, and solar heaters.

10. The system for fluid sterilization as defined in claim 1, further comprising an autoclave coupled to the heating section to receive pressurized fluid outflow therefrom, the autoclave chamber having an enclosure for receiving an item for sterilization, which can be flooded with the pressurized fluid received from the heating section for sterilization.

11. A system for fluid sterilization, comprising:
an inlet for operative connection to a fluid source to provide fluid along a flow path for sterilization by the system;
a heating section in fluid communication with the inlet along the flow path, the heating section heats pressurized fluid therein above prescribed thresholds for temperature, pressure, and dwell time to achieve a desired level of sterilization;
a heat exchanger having a first path disposed in fluid communication between the inlet and the heating section along the flow path to preheat fluid prior to entering the heating section and having a second path positioned between the heating section and a system outlet along the flow path to cool outflow of the heating section prior to exiting the outlet, wherein the first path and the second path of the heat exchanger are configured to pass heat energy therebetween; and
a plurality of valves disposed along the flow path, wherein the plurality of valves includes
(a) a first valve downstream of the inlet and upstream of the first path of the heat exchanger,
(b) a second valve downstream of the first path of the heat exchanger and upstream of the heating section,
(c) a third valve downstream of the heating section and upstream of the second path of the heat exchanger, and
(d) a fourth valve downstream of the second path of heat exchanger and upstream of the outlet;
a plurality of sensors disposed along the flow path, including (a) a pressure sensor disposed downstream of the inlet and upstream of the first path of the heat exchanger, (b) temperature sensors disposed in the heating section to measure fluid temperature therein, (c) a pressure sensor disposed downstream of the second path of the heat exchanger and upstream of the outlet; and (d) a temperature sensor disposed downstream of the second path of the heat exchanger and upstream of the outlet;
a digital controller in operative communication with the plurality of sensors to receive measurements therefrom and in operative control of the plurality of valves to operate the valves in a controlled sequence to facilitate flow through the system while controlling to prescribed pressure and temperature profiles across prescribed ranges for pressure and temperature to achieve the desired level of sterilization without need of maintaining a fixed temperature or a fixed pressure within the heating section.

12. The system for fluid sterilization as defined in claim 11, wherein the heating section comprise turbulence generators to create turbulent flow of fluid therein proximate to heaters therein.

13. The system for fluid sterilization as defined in claim 11, further comprising an autoclave coupled to the heating section to receive pressurized fluid outflow therefrom, the autoclave chamber having an enclosure for receiving an item for sterilization, which can be flooded with the pressurized fluid received from the heating section for sterilization.

14. The system for fluid sterilization as defined in claim 13, wherein the autoclave is disposed along the flow path downstream of the heating section and upstream of the second path of the heat exchanger.

15. The system for fluid sterilization as defined in claim 13, wherein the autoclave includes a heating assembly therein.

16. The system for fluid sterilization as defined in claim 11, wherein the heating section comprises a distillation component is disposed along the flow path, in which fluid vaporizes when it enters a low pressure zone therein, the vaporized fluid collects as distillate at a condenser before continuing downstream along the flow path.

17. The system for fluid sterilization as defined in claim 11, wherein the heating section comprises a heat source selected from a group consisting of inductive heat exchanger and surface heat exchanger.

18. The system for fluid sterilization as defined in claim 11, wherein the flow path comprises parallel paths through the heating section.

19. The system for fluid sterilization as defined in claim 11, wherein the heating section is integrated within a combined heat and power system wherein the heat supply for the sterilization of the fluid is supplied by heat produced within the electric power generator system.

20. The system for fluid sterilization as defined in claim 11, wherein the heating section is integrated with a solar electric power generating system wherein the heat supply for the sterilization is provided by heat produced within the solar power system.

* * * * *